United States Patent [19]

Chakravarty et al.

[11] Patent Number: 5,559,128
[45] Date of Patent: Sep. 24, 1996

[54] 3-SUBSTITUTED PIPERIDINES PROMOTE RELEASE OF GROWTH HORMONE

[75] Inventors: Prasun K. Chakravarty, Edison; Ravi Nargund, East Brunswick; Robert W. Marquis, Iselin; Arthur A. Patchett, Westfield; Lihu Yang, Edison, all of N.J.

[73] Assignee: Merck & Co., Inc., Rahway, N.J.

[21] Appl. No.: 424,750

[22] Filed: Apr. 18, 1995

[51] Int. Cl.⁶ .................... A61K 31/445; C07D 401/06; C07D 209/04

[52] U.S. Cl. .................. 514/323; 514/256; 514/318; 514/319; 514/322; 514/324; 514/326; 514/362; 514/363; 514/365; 514/372; 514/394; 514/396; 514/414; 514/300; 514/314; 540/596; 540/597; 540/598; 540/601; 540/603; 540/607; 544/335; 546/113; 546/152; 546/172; 546/193; 546/199; 546/201; 546/202; 546/205; 546/209; 546/210

[58] Field of Search .................... 840/596, 597, 840/598, 601, 603, 607; 544/335; 546/193, 199, 201, 202, 205, 209, 210, 113, 172, 152; 548/127, 128, 205, 214, 253, 306, 467, 468; 514/256, 318, 319, 322, 323, 324, 326, 362, 363, 365, 372, 394, 396, 414, 300, 314

[56] References Cited

U.S. PATENT DOCUMENTS

| | | | |
|---|---|---|---|
| 3,239,345 | 3/1966 | Hodge et al. | 514/450 |
| 4,036,979 | 7/1977 | Asato | 514/443 |
| 4,411,890 | 10/1983 | Momany | 514/17 |
| 4,782,139 | 11/1988 | Dimarchi et al. | 530/407 |
| 5,137,872 | 8/1992 | Seely, et al. | 514/12 |
| 5,164,368 | 11/1992 | Recker | 514/12 |
| 5,206,235 | 4/1993 | Fisher et al. | 514/213 |
| 5,283,241 | 2/1994 | Bochis et al. | 514/183 |
| 5,284,841 | 2/1994 | Chu et al. | 514/183 |
| 5,310,737 | 5/1994 | Fisher et al. | 514/215 |
| 5,317,017 | 5/1994 | Ok et al. | 514/211 |

FOREIGN PATENT DOCUMENTS

| | | |
|---|---|---|
| 0144230A3 | 6/1985 | European Pat. Off. . |
| 5163224 | 12/1994 | Japan . |
| WO94/08583 | 4/1994 | WIPO . |
| WO94/07486 | 4/1994 | WIPO . |
| WO94/13696 | 6/1994 | WIPO . |
| WO94/19367 | 9/1994 | WIPO . |
| WO95/13069 | 5/1995 | WIPO . |

OTHER PUBLICATIONS

Sakamoto, et al., *Chem. Abstracts*, 113(9) 73,560u (1990).
Horwell, et al., *Chem. Abstracts*, 113 (15) 132,771p (1990).
R. G. Smith, et al., *Science*, Reprint Series, 11 Jun. (1993), vol. 260, pp. 1640–1643 "A Nonpeptidyl Growth Hormone Secretagogue".
Essawi et al. "Synthesis and Evaluation of 1– and 2–substituted fentanyl analogues for opioid activity" *J. Med. Chem.* v. 26, p. 348–352 (1983).

*Primary Examiner*—Ceila Chang
*Attorney, Agent, or Firm*—J. Eric Thies; David L. Rose

[57] ABSTRACT

The present invention is directed to certain novel compounds identified as 3-substituted piperidines of the general structural formula:

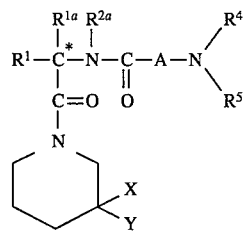

wherein $R^1$, $R^{1a}$, $R^{2a}$, $R^4$, $R^5$, A, X, and Y are as defined herein. These compounds promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by the anabolic effects of growth hormone. Growth hormone releasing compositions containing these compounds as the active ingredient thereof are also disclosed.

8 Claims, No Drawings

3-SUBSTITUTED PIPERIDINES PROMOTE RELEASE OF GROWTH HORMONE

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carded with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray. Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. Non peptidal growth hormone secretagogues with a benzolactam structure are disclosed in e.g., U.S. Pat. Nos. 5,206,235, 5,283,241, 5,284,841, 5,310,737 and 5,317,017. Other growth hormone secretagogues are disclosed in PCT Patent Publications WO 94/13696 and WO 94/19367. The instant compounds are low molecular weight peptide analogs for promoting the release of growth hormone which have good stability in a variety of physiological environments and which may be administered parenterally, nasally or by the oral route.

SUMMARY OF THE INVENTION

The instant invention is directed to certain 3-substituted piperidine compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food or wool production where the stimulation of growth hormone will result in a larger, more productive animal. Thus, it is an object of the instant invention to describe the 3-substituted piperidine compounds. It is a further object of this invention to describe procedures for the preparation of such compounds. A still further object is to describe the use of such compounds to increase the secretion of growth hormone in humans and animals. A still further object of this invention is to describe compositions containing the 3-substituted pipeddine compounds for the use of treating humans and animals so as to increase the level of growth hormone secretions. Further objects will become apparent from a reading of the following description.

DESCRIPTION OF THE INVENTION

The novel 3-substituted piperidines of the instant invention are described by structural Formula I:

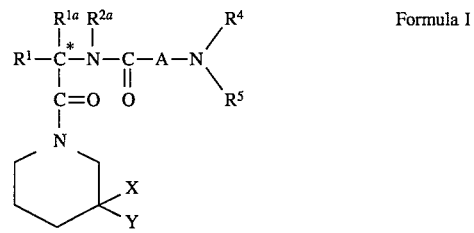

Formula I wherein:

$R^1$ is selected from the group consisting of: $C_1$–$C_{10}$ alkyl, aryl, aryl($C_1$–$C_6$ alkyl), ($C_3$–$C_7$ cycloalkyl)($C_1$–$C_6$ alkyl)-, ($C_1$–$C_5$ alkyl)-K-($C_1$–$C_5$ alkyl)-, aryl($C_0$–$C_5$ alkyl)-K-($C_1$–$C_5$ alkyl)-, and ($C_3$–$C_7$ cycloalkyl)($C_0$–$C_5$ alkyl)-K-($C_1$–$C_5$ alkyl)-, where K is —O—, —S(O)$_m$—, —N(R$^2$)C(O)—, —C(O)N(R$^2$)—, —OC(O)—, —C(O)O—, —CR$^2$=CR$^2$—, or —C≡C—, where aryl is selected from: phenyl, naphthyl, indolyl, azaindole, pyridyl, benzothienyl, benzofuranyl, thiazolyl, and benzimidazolyl, and $R^2$ and alkyl may be further substituted by 1 to 9 halogen, S(O)$_m$R$^{2a}$, 1 to 3 of OR$^{2a}$ or C(O)OR$^{2a}$, and aryl may be further substituted by 1 to 3 of $C_1$–$C_6$ alkyl, 1 to 3 of halogen, 1 to 2 of —OR$^2$, methylenedioxy, —S(O)$_m$R$^2$, 1 to 2 of —CF$_3$, —OCF$_3$, nitro, —N(R$^2$)C(O)(R$^2$), —C(O)OR$^2$, —C(O)N(R$^2$)(R$^2$), —1H-tetrazol-5-yl, —SO$_2$N(R$^2$)(R$^2$), —N(R$^2$)SO$_2$phenyl, or —N(R$^2$)SO$_2$R$^2$;

$R^{1a}$ is selected from hydrogen and $C_1$–$C_6$ alkyl;

$R^2$ is selected from: hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring, optionally including oxygen, sulfur or NR$^{3a}$, where R$^{3a}$ is hydrogen, or $C_1$–$C_6$ alkyl, optionally substituted by hydroxyl;

$R^{2a}$ is selected from hydrogen and $C_1$–$C_6$ alkyl;

$R^4$ and $R^5$ are independently hydrogen, $C_1$–$C_6$ alkyl, or substituted $C_1$–$C_6$ alkyl where the substituents are selected from: 1 to 5 halo, 1 to 3 hydroxy, 1 to 3 $C_1$–$C_{10}$ alkanoyloxy, 1 to 3 $C_1$–$C_6$ alkoxy, phenyl, phenyloxy, 2-furyl, $C_1$–$C_6$ alkoxycarbonyl, S(O)$_m$($C_1$–$C_6$ alkyl), or $R^4$ and $R^5$ may be taken together to form —(CH$_2$)$_d$—L$_a$(CH$_2$)$_e$— where L$_a$ is —C(R$^2$)$_2$—, —O—, —S(O)$_m$— or —N(R$^2$)—, d and e are independently 1 to 3 and R$^2$ is as defined above;

X is selected from the group consisting of: —(CH$_2$)$_q$N(R$^8$)C(O)R$^2$, —(CH$_2$)$_q$N(R$^8$)C(O)R$^8$, —$(CH_2)_qN(R^8)C(O)OR^2$, —$(CH_2)_qN(R^8)C(O)OR^8$,
—$(CH_2)_qN(R^8)C(O)OR^2$, —$(CH_2)_qN(R^2)C(O)OR^8$,
—$(CH_2)_qN(R^8)C(O)OR^8$, —$(CH_2)_qN(R^2)SO_2R^9$,
—$(CH_2)_q N(R^8)SO_2R^8$, —$(CH_2)_qN(R^8)SO_2R^2$,
—$(CH_2)_qN(R^2)SO_2N(R^2)(R^2)$,
—$(CH_2)_qN(R^2)SO_2N(R^2)(R^8)$,
—$(CH_2)_qN(R^8)C(O)N(R^2)(R^2)$,
—$(CH_2)_qN(R^8)C(O)N(R^2)(R^8)$,
—$(CH_2)_qSO_2N(R^2)(R^2)$, —$(CH_2)_qSO_2N(R^2)(R^8)$,
—$(CH_2)_qN(R^2)(R^8)$, and —$(CH_2)_q R^{10}$, where the $R^2$ and $(CH_2)_q$ groups may be optionally substituted by 1 to 2 $C_1$–$C_4$ alkyl, hydroxyl, $C_1$–$C_4$ lower alkoxy, carboxyl, $CONH_2$, $S(O)_mCH_3$, carboxylate $C_1$–$C_4$ alkyl esters, or 1H-tetrazol-5-yl;

Y is selected from the group consisting of: hydrogen, $C_1$–$C_{10}$ alkyl, —$(CH_2)_q$aryl, —$(CH_2)_q(C_3$–$C_7$ cycloalkyl), —$(CH_2)_q$—K—$(C_1$–$C_6$ alkyl), —$(CH_2)_q$—K—$(CH_2)_t$aryl, —$(CH_2)_q$—K—$(CH_2)_t(C_3$–$C_7$ cycloalkyl containing O—, —$NR^2$—, or —S—), and —$(CH_2)_q$—K—$(CH_2)_t(C_3$–$C_7$ cycloalkyl), where K is as defined above, and where the alkyl, $R^2$, $(CH_2)_q$ and $(CH_2)_t$ groups may be optionally substituted by $C_1$–$C_4$ alkyl, hydroxyl, $C_1$–$C_4$ lower alkoxy, carboxyl, —$CONH_2$ or carboxylate $C_1$–$C_4$ alkyl esters, and where aryl is phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrazinyl, or isothiazolyl which is optionally substituted by 1 to 3 halogen, 1 to 3 —$OR^2$, —$C(O)OR^2$, —$C(O)N(R^2)(R^2)$, nitro, cyano, benzyl, 1 to 3 $C_1$–$C_4$ alkyl, —$S(O)_mR^2$, or 1H-tetrazol-5-yl;

A is:

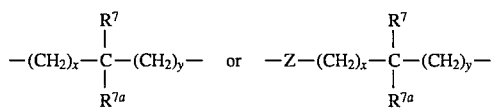

where x and y are independently 0, 1, 2 or 3;

Z is —$N(R^{6a})$— or —O—, where $R^{6a}$ is hydrogen or $C_1$–$C_6$ alkyl;

$R^7$ and $R^{7a}$ are independently hydrogen, $C_1$–$C_6$ alkyl, trifluoromethyl, phenyl, or substituted $C_1$–$C_6$ alkyl where the substituents are imidazolyl, naphthyl, phenyl, indolyl, p-hydroxyphenyl, —$OR^2$, —$S(O)_mR^2$, —$C(O)OR^2$, $C_3$–$C_7$ cycloalkyl, —$N(R^2)(R^2)$, —$C(O)N(R^2)(R^2)$, or $R^7$ and $R^{7a}$ may independently be joined to one or both of $R^4$ and $R^5$ groups to form an alkylene bridge between the terminal nitrogen and the alkyl portion of the $R^7$ or $R^{7a}$ groups, wherein the bridge contains 1 to 5 carbons atoms, or $R^7$ and $R^{7a}$ can be joined to one another to form $C_3$–$C_7$ cycloalkyl;

$R^8$ is —$(CH_2)_p$aryl, where aryl is selected from: phenyl, naphthyl, pyridyl, thiazolyl, isothiazolyl, oxazolyl, isoxazolyl, thienyl, pyrazinyl, pyrimidinyl, benzothienyl, benzofuranyl, benzimidazolyl, imidazolyl, indolyl, quinolinyl, and isoquinolinyl, and where the aryl is optionally substituted with 1 to 2 of halogen, —$R^2$, —$OR^2$, —$N(R^2)(R^2)$, —$C(O)OR^2$, or —$C(O)N(R^2)(R^2)$;

$R^9$ is selected from the group consisting of: isoxazolyl, thiazolyl, isothiazolyl, thienyl, benzothienyl, benzofuranyl, benzimidazolyl, imidazolyl, indolyl, quinolinyl, and isoquinolinyl, which are optionally substituted by 1 to 2 of halogen, —$R^2$, —$OR^2$, —$N(R^2)(R^2)$, —$C(O)OR^2$, or —$C(O)N(R^2)(R^2)$;

$R^{10}$ is selected from the group consisting of: 1,2,4-oxadiazolyl, pyrazinyl, triazolyl, and phthalimidoyl, which are optionally substituted with —$R^2$, —$OR^2$ or —$N(R^2)(R^2)$;

m is 0, 1, or 2;

p is 0, 1, 2, or 3;

q is 0, 1, 2, 3, or 4;

t is 0, 1, 2, or 3;

and pharmaceutically acceptable salts and individual diastereomers thereof.

In the above structural formula and throughout the instant specification, the following terms have the indicated meanings:

The alkyl groups specified above are intended to include those alkyl groups of the designated length in either a straight or branched configuration and if two carbon atoms or more they may include a double or a triple bond. Exemplary of such alkyl groups are methyl, ethyl, propyl, isopropyl, butyl, sec-butyl, tertiary butyl, pentyl, isopentyl, hexyl, isohexyl, allyl, propargyl, and the like.

The alkoxy groups specified above are intended to include those alkoxy groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term "halogen" is intended to include the halogen atom fluorine, chlorine, bromine and iodine.

The term "aryl" within the present invention, unless otherwise specified, is intended to include aromatic rings, such as carbocyclic and heterocyclic aromatic rings selected the group consisting of: phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, or isothiazolyl, which may be optionally substituted by 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, —1H-tetrazol-5-yl, —$SO_2N(R^2)(R^2)$, —$N(R^2)SO_2$ phenyl, or —$N(R^2)SO_2R^2$, wherein $R^2$ is as defined herein.

Certain of the above defined terms may occur more than once in the above formula and upon such occurrence each term shall be defined independently of the other.

Preferred compounds of the instant invention include those of Formula Ia:

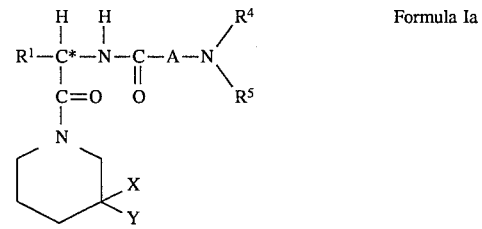

Formula Ia wherein:

$R^1$ is selected from the group consisting of: $C_1$–$C_{10}$ alkyl, aryl ($C_1$–$C_4$ alkyl)-, $C_3$–$C_6$ cycloalkyl ($C_1$–$C_4$ alkyl)-, ($C_1$–$C_4$ alkyl)-K-($C_1$–$C_2$ alkyl)-, aryl ($C_0$–$C_2$ alkyl)-K-($C_1$–$C_2$ alkyl)-, and ($C_3$–$C_7$ cycloalkyl)($C_0$–$C_2$ alkyl)-K-($C_1$–$C_2$ alkyl)-, where K is —O—, —$S(O)_m$—, —OC(O)—, or —C(O)O—, and the alkyl groups may be further substituted by 1 to 7 halogen, —$S(O)_mR^2$, 1 to 3 —$OR^2$ or —$C(O)OR^2$, and aryl is phenyl, naphthyl, indolyl, pyridyl, benzimidazolyl, azaindolyl, benzothienyl or benzofuranyl which may be further substituted by 1–2 $C_1$–$C_4$ alkyl, 1 to 2 halogen, 1 to 2 —$OR^2$, —$S(O)_mR^2$, or —$C(O)OR^2$;

$R^2$ is hydrogen, $C_1$–$C_6$ alkyl, or $C_3$–$C_7$ cycloalkyl, and where two $C_1$–$C_6$ alkyl groups are present on one atom they may be optionally joined to form a $C_4$–$C_7$ cyclic ring optionally including oxygen, sulfur or $NR^{3a}$;

$R^4$ and $R^5$ are independently hydrogen, $C_1$–$C_6$ alkyl, or substituted $C_1$–$C_6$ alkyl where the substituents are 1 to 5 halo, 1 to 3 hydroxyl, —$S(O)_m$ ($C_1$–$C_6$ alkyl) or phenyl;

X is selected from the group consisting of: —$(CH_2)_qN(R^8)C(O)R^2$, —$(CH_2)_qN(R^8)C(O)R^8$, —$(CH_2)_qN(R^8)C(O)OR^2$, —$(CH_2)_qN(R^8)C(O)OR^8$, —$(CH_2)_qN(R^8)C(O)OR^2$, —$(CH_2)_qN(R^2)C(O)OR^8$, —$(CH_2)_qN(R^8)C(O)OR^8$, —$(CH_2)_qN(R^2)SO_2R^9$, —$(CH_2)_q N(R^8)SO_2R^8$, —$(CH_2)_qN(R^8)SO_2R^2$, —$(CH_2)_qN(R^2)SO_2N(R^2)(R^2)$, —$(CH_2)_qN(R^2)SO_2N(R^2)(R^8)$, —$(CH_2)_qN(R^8)C(O)N(R^2)(R^2)$, —$(CH_2)_qN(R^8)C(O)N(R^2)(R^8)$, —$(CH_2)_qSO_2N(R^2)(R^2)$, —$(CH_2)_qSO_2N(R^2)(R^8)$, —$(CH_2)_qN(R^2)(R^8)$, and —$(CH_2)_qR^{10}$, where the $R^2$, and $(CH_2)_q$ groups are optionally substituted by 1 to 2 $C_1$–$C_4$ alkyl, hydroxyl, $C_1$–$C_4$ lower alkoxy, carboxyl, $CONH_2$, $S(O)_mCH_3$, carboxylate $C_1$–$C_4$ alkyl esters, or 1H-tetrazol-5-yl;

Y is selected from the group consisting of: hydrogen, $C_1$–$C_8$ alkyl, $(CH_2)_t$aryl, —$(CH_2)_q(C_5$–$C_6$ cycloalkyl), —$(CH_2)_q$—K—$(C_1$–$C_6$ alkyl), —$(CH_2)_q$—K—$(CH_2)_t$aryl, —$(CH_2)_q$—$(CH_2)_t(C_3$–$C_7$ cycloalkyl containing —O—, —$NR^2$—, or —S—), and —$(CH_2)_q$—K—$(CH_2)_t$ ($C_5$–$C_6$ cycloalkyl), where K is —O— or —$S(O)_m$— and where the alkyl groups are optionally substituted by hydroxyl, carboxyl, $CONH_2$, carboxylate $C_1$–$C_4$ alkyl esters or 1H-tetrazole-5-yl and aryl is phenyl, naphthyl, pyridyl, 1-H-tetrazolyl, thiazolyl, imidazolyl, indolyl, pyrimidinyl, thiadiazolyl, pyrazolyl, oxazolyl, isoxazolyl, or thiophenyl which is optionally substituted by 1 to 3 halogen, 1 to 3 —$OR^2$, —$C(O)OR^2$, —$C(O)N(R^2)(R^2)$, cyano, 1 to 2 $C_1$–$C_4$ alkyl, benzyl, —$S(O)_mR^2$, or 1H-tetrazol-5-yl-;

A is:

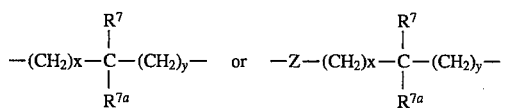

where x and y are independently 0, 1 or 2;

Z is —$NR^{6a}$— or —O—, where $R^{6a}$ is hydrogen or $C_1$–$C_3$ alkyl;

$R^7$ and $R^{7a}$ are independently hydrogen $C_1$–$C_6$ alkyl, trifluoromethyl, phenyl, substituted $C_1$–$C_6$ alkyl where the substituents are imidazolyl, naphthyl, phenyl, indolyl, p-hydroxyphenyl, $OR^2$, $S(O)_mR^2$, $C(O)OR^2$, $C_5$–$C_7$ cycloalkyl, —$N(R^2)(R^2)$, —$C(O)N(R^2)(R^2)$; or $R^7$ and $R^{7a}$ can independently be joined to one of $R^4$ or $R^5$ to form alkylene bridges between the terminal nitrogen and the alkyl portion of $R^7$ or $R^{7a}$ groups to form 5 or 6 membered rings; or $R^7$ and $R^{7a}$ can be joined to one another to form a $C_3$ cycloalkyl;

$R^8$ is —$(CH_2)_p$aryl, where aryl is selected from: phenyl, naphthyl, pyridyl, thiazolyl, isothiazolyl, oxazolyl, isoxazolyl, thienyl, pyrazinyl, pyrimidinyl, benzothienyl, benzofuranyl, benzimidazolyl, imidazolyl, indolyl, quinolinyl, and isoquinolinyl, and where aryl may be substituted by 1 to 2 of halogen, —$R^2$, —$OR^2$, —$N(R^2)(R^2)$, —$C(O)OR^2$, or —$C(O)N(R^2)(R^2)$;

$R^9$ is selected from the group consisting of: isoxazolyl, thiazolyl, isothiazolyl, thienyl, benzothienyl, benzofuranyl, benzimidazolyl, imidazolyl, indolyl, quinolinyl, and isoquinolinyl, which may be substituted by 1 to 2 of halogen, —$R^2$, —$OR^2$, —$N(R^2)(R^2)$, —$C(O)OR^2$, or —$C(O)N(R^2)(R^2)$;

$R^{10}$ is selected from the group consisting of: 1,2,4-oxadiazolyl, pyrazinyl, triazolyl, and phthalimidoyl, which are optionally substituted with —$R^2$, —$OR^2$ or —$N(R^2)(R^2)$;

m is 0, 1 or 2;

p is 0, 1 or 2;

q is 0, 1 or 2;

t is 0, 1 or 2;

and pharmaceutically acceptable salts and individual diastereomers thereof.

More preferred compounds of the instant invention include those of Formula Ib:

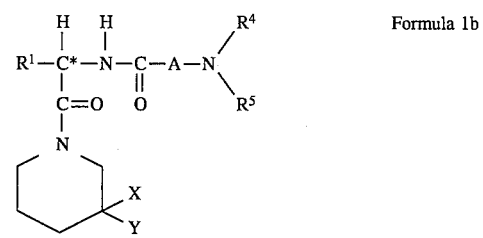

Formula Ib wherein:

$R^1$ is selected from the group consisting of: $C_1$–$C_{10}$ alkyl, aryl ($C_1$–$C_3$ alkyl)-, ($C_3$–$C_7$ cycloalkyl)($C_1$–$C_3$ alkyl)-, and aryl ($C_0$–$C_1$ alkyl)-K-($C_1$–$C_2$ alkyl)-, where K is O or $S(O)_m$ and the aryl is phenyl, pyridyl, naphthyl, indolyl, azaindolyl, benzothienyl, or benzimidazolyl which is optionally substituted by 1–2 $C_1$–$C_4$ alkyl, 1 to 2 halogen, 1 to 2 —$OR^2$, —$S(O)_mR^2$, or $C(O)OR^2$;

$R^2$ is hydrogen, $C_1$–$C_6$ alkyl, or $C_3$–$C_7$ cycloalkyl, and where two $C_1$–$C_6$ alkyl groups are present on one atom they may be optionally joined to form a $C_5$–$C_7$ cyclic ring optionally including oxygen, sulfur or $NR^{3a}$;

$R^4$ and $R^5$ are independently hydrogen, $C_1$–$C_4$ alkyl, or substituted $C_1$–$C_3$ alkyl where the substituents may be 1 to 2 hydroxyl;

X is selected from the group consisting of: —$(CH_2)_qN(R^8)C(O)R^2$, —$(CH_2)_qN(R^8)C(O)R^8$, —$(CH_2)_qN(R^8)C(O)OR^2$, —$(CH_2)_qN(R^8)C(O)OR^8$, —$(CH_2)_qN(R^8)C(O)OR^2$, —$(CH_2)_qN(R^8)C(O)OR^8$, —$(CH_2)_qN(R^2)SO_2R^9$, —$(CH_2)_qN(R^8)SO_2R^8$, $(CH_2)_qN(R^8)SO_2R^2$, —$(CH_2)_qN(R^8)C(O)N(R^2)(R^2)$, —$(CH_2)_qN(R^8)C(O)N(R^2)(R^8)$, —$(CH_2)_qSO_2N(R^2)(R^2)$, —$(CH_2)_qSO_2N(R^2)(R^8)$, —$(CH_2)_qN(R^2)(R^8)$, and —$(CH_2)_qR^{10}$, where the $R^2$, and $(CH_2)_q$ groups may be optionally substituted by 1 to 2 $C_1$–$C_4$ alkyl, hydroxyl, $C_1$–$C_4$ lower alkoxy, carboxyl, —$CONH_2$, —$S(O)_mCH_3$, carboxylate $C_1$–$C_4$ alkyl esters, or 1H-tetrazol-5-yl;

Y is selected from the group consisting of: hydrogen, $C_1$–$C_8$ alkyl, $(CH_2)_t$aryl, —$(CH_2)_q$ $C_5$–$C_7$ cycloalkyl, —$(CH_2)_q$—K—$(C_1$–$C_6$ alkyl), —$(CH_2)_q$—K—$(CH_2)_t$aryl, and —$(CH_2)_q$—$(CH_2)_t$ ($C_5$–$C_6$ cycloalkyl), where K is $S(O)_m$ and where the alkyl groups may be optionally substituted by hydroxyl, carboxyl, $CONH_2$, carboxylate $C_1$–$C_4$ alkyl esters or 1H-tetrazole-5-yl and aryl is phenyl, naphthyl, indolyl, pyridyl, thiazolyl, thiopheneyl, pyrazolyl, oxazolyl, isoxazolyl or imidazolyl which may be optionally substituted by 1 to 2 halogen, 1 to 2 —$OR_2$, 1 to 2 —$N(R^2)(R^2)$, —$CO(OR^2)$, 1 to 2 $C_1$–$C_4$ alkyl, —$S(O)_mR^2$, or 1H-tetrazol-5-yl;

A is:

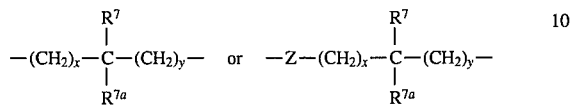

where x and y are independantly 0 or 1;

Z is —$N(R^{6a})$— or —O—, where $R^{6a}$ is hydrogen or $C_1$–$C_3$ alkyl;

$R^7$ and $R^{7a}$ are independently hydrogen, $C_1$–$C_6$ alkyl, phenyl, substituted $C_1$–$C_6$ alkyl wherein the substitutent is imidazolyl, naphthyl, phenyl, indolyl, p-hydroxyphenyl, —$OR^2$, —$S(O)_mR^2$, or $R^7$ and $R^{7a}$ can independently be joined to one of $R^4$ or $R^5$ to form alkylene bridges between the terminal nitrogen and the alkyl portions of $R^7$ or $R^{7a}$ groups to form 5 or 6 membered rings; or $R^7$ or $R^{7a}$ can be joined to one another to form a $C_3$–$C_6$ cycloalkyl;

$R^8$ is —$(CH_2)_p$aryl, where aryl is selected from: phenyl, naphthyl, pyridyl, thiazolyl, isothiazolyl, oxaxolyl, isoxazolyl, thienyl, pyrazinyl, pyrimidinyl, benzothienyl, benzofuranyl, benzimidazolyl, imidazolyl, indolyl, quinolinyl, and isoquinolinyl, and where aryl may be substituted by 1 to 2 of halogen, —$R^2$, —$OR^2$, —$N(R^2)(R^2)$, —$C(O)OR^2$, or —$C(O)N(R^2)(R^2)$;

$R^9$ is selected from the group consisting of: isoxazolyl, thiazolyl, isothiazolyl, indolyl, thienyl, benzothienyl, benzofuranyl, benzimidazolyl, imidazolyl, quinolinyl, and isoquinolinyl, which may be substituted by 1 to 2 of halogen, —$R^2$, —$OR^2$, —$N(R^2)(R^2)$, —$C(O)OR^2$, or —$C(O)N(R^2)(R^2)$;

$R^{10}$ is selected form the group consisting of: 1,2,4-oxadiazolyl, pyrazinyl, and triazolyl which may be substituted by —$R^2$, —$OR^2$, or —$N(R^2)(R^2)$;

m is 0, 1, or 2;

p is 0,1, or 2 q is 0, 1,or 2;

t is 0, 1, or 2;

and pharmaceutically acceptable salts and individual diastereomers thereof.

Still more preferred compounds of the instant invention include those of Formula Ic:

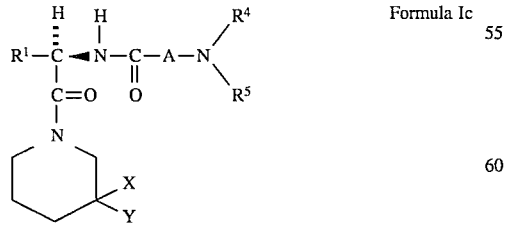

Formula Ic wherein:

$R^1$ is selected from the group consisting of:

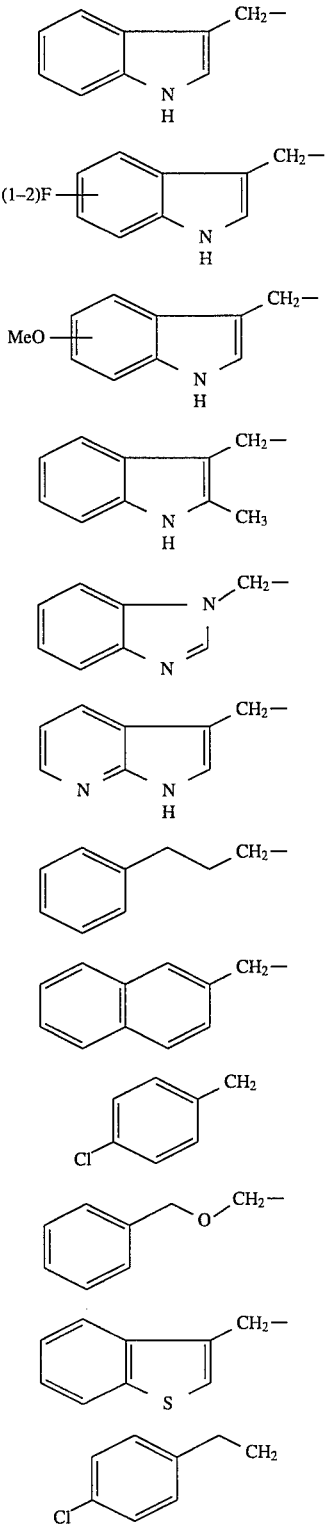

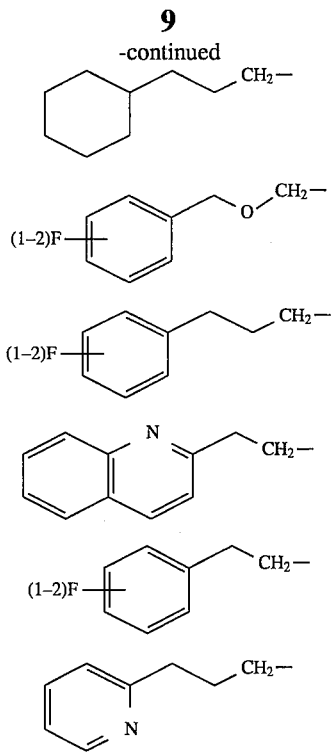

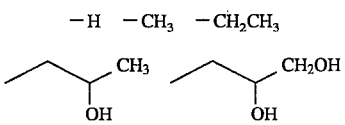

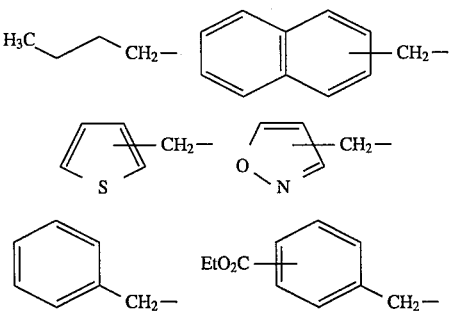

or their regioisomers where not specified;

$R^2$ is hydrogen, $C_1$–$C_6$ alkyl, or $C_3$–$C_7$ cycloalkyl and where two $C_1$–$C_6$ alkyl groups are present on one atom they may be optionally joined to form a $C_5$–$C_7$ cyclic ring optionally including oxygen, sulfur or $NR_{3a}$;

$R^4$ and $R^5$ are independently selected from the group consisting of:

–H  –CH$_3$  –CH$_2$CH$_3$

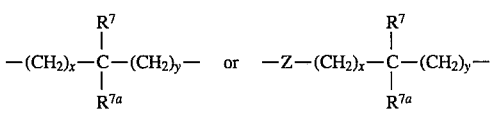

X is selected from the group consisting of:
—(CH$_2$)$_q$N(R$^8$)C(O)R$^2$,  —(CH$_2$)$_q$N(R$^8$)C(O)R$^8$,
—(CH$_2$)$_q$N(R$^8$)C(O)OR$^2$,  —(CH$_2$)$_q$N(R$^2$)C(O)OR$^8$,
—(CH$_2$)$_q$N(R$^8$)C(O)OR$^8$,  —(CH$_2$)$_q$N(R$^2$)SO$_2$R$^9$,
—(CH$_2$)$_q$N(R$^8$)SO$_2$R$^8$,  —(CH$_2$)$_q$N(R$^8$)SO$_2$R$^2$,
—(CH$_2$)$_q$N(R$^2$)SO$_2$N(R$^2$)(R$^2$),
—(CH$_2$)$_q$N(R$^2$)SO$_2$N(R$^2$)(R$^8$),
—(CH$_2$)$_q$N(R$^8$)C(O)N(R$^2$)(R$^2$),
—(CH$_2$)$_q$N(R$^8$)C(O)N(R$^2$)(R$^8$), and —(CH$_2$)$_q$N(R$^2$)(R$^8$);

Y is selected from the group consisting of: hydrogen,

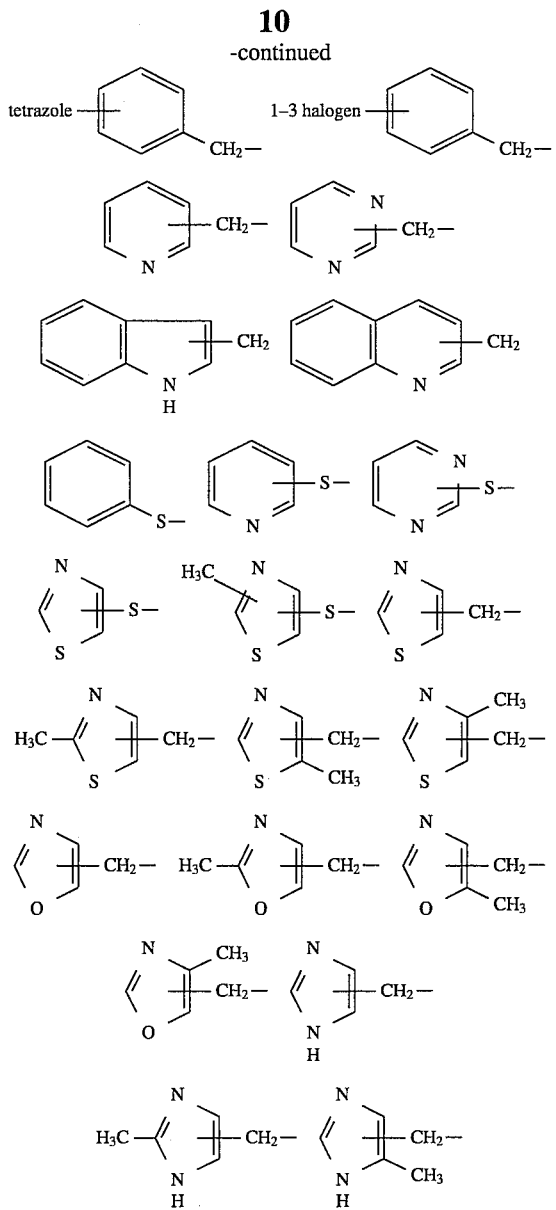

or their regioisomers whereof where not specified;

A is:

$$-(CH_2)_x-\underset{R^{7a}}{\overset{R^7}{C}}-(CH_2)_y- \quad \text{or} \quad -Z-(CH_2)_x-\underset{R^{7a}}{\overset{R^7}{C}}-(CH_2)_y-$$

where x and y are independently 0 or 1;

Z is —(NR$^{6a}$)— or —O—, where R$^{6a}$ is hydrogen or $C_1$–$C_6$ alkyl;

$R^7$ and $R^{7a}$ are independently $C_1$–$C_6$ alkyl and substituted $C_1$–$C_6$ alkyl wherein the substituent is phenyl, naphthyl or indolyl or $R^7$ and $R^{7a}$ can independently be joined to one of the $R^4$ or $R^5$ to form alkylene bridges between the terminal nitrogen and the alkyl portions of $R^7$ or $R^{7a}$ to form 5 or 6 membered rings;

$R^8$ is (CH$_2$)$_p$aryl where aryl is selected from: phenyl, naphthyl, pyridyl, pyrazinyl, pyrimidinyl, thiazolyl, indolyl, quinolinyl and isoquinolinyl and where the aryl may be substituted by 1 to 2 halogen, —R$^2$, —OR$^2$, N(R$^2$)(R$^2$), —C(O)OR$^2$ or —C(O)N(R$^2$)(R$^2$);

$R^9$ is selected from the group consisting of: isoxazolyl, thiazolyl, indolyl, quinolinyl and isoquinolinyl, which may be substituted by 1 to 2 halogen, $-R^2$, $-OR^2$, $-N(R^2)(R^2)$, $-C(O)OR^2$ or $-C(O)N(R^2)(R^2)$;

$R^{10}$ is 1,2,4-oxadiazolyl which may be substituted by $-R^2$, $-OR^2$, or $-N(R^2)(R^2)$;

m is 0, 1 or 2;

p is 0 or 1;

q is 0 or 1;

t is 0 or 1;

and pharmaceutically acceptable salts and individual diasteromers thereof.

The most preferred compounds of the instant invention include those of Formula Id:

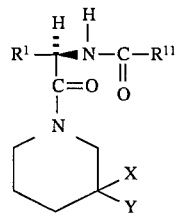

Formula Id wherein:

$R^1$ is selected from the group consisting of:

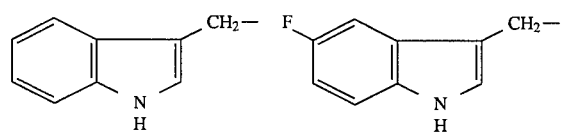

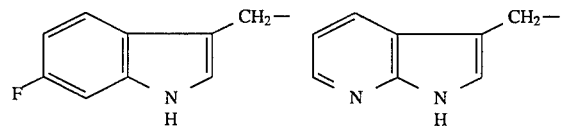

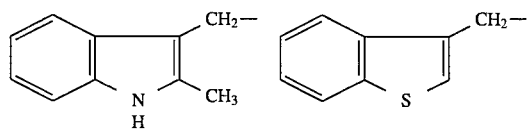

X is selected from the group consisting of:

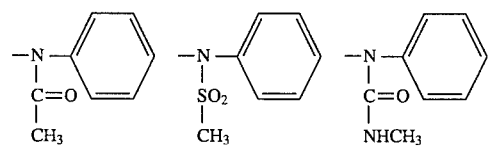

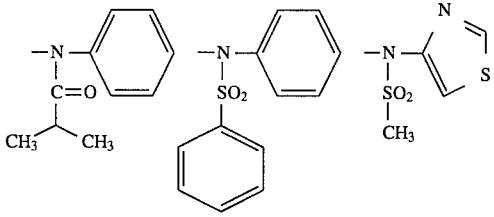

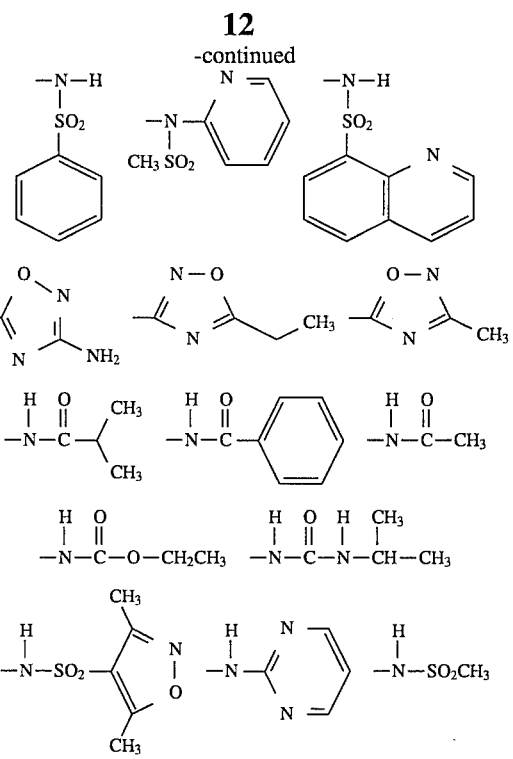

Y is selected from the group consisting of: hydrogen,

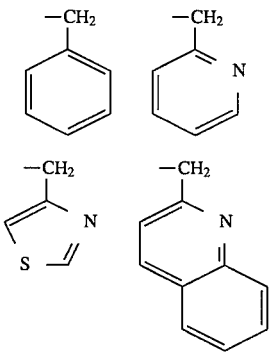

$R^{11}$ is selected from the group consisting of:

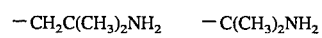

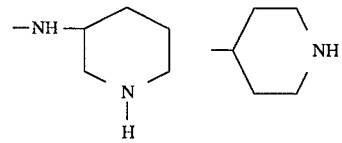

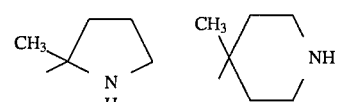

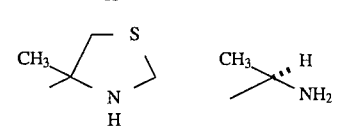

and pharmaceutically acceptable salts and individual diasteromers thereof.

Throughout the instant application, the following abbreviations are used with the following meanings:

| | |
|---|---|
| Bu | butyl |
| Bn | benzyl |
| BOC, Boc | t-butyloxycarbonyl |
| BOP | Benzotriazol-1-yloxy tris/dimethylamino)-phosphonium hexafluorophosphate |
| calc. | calculated |
| CBZ, Cbz | Benzyloxycarbonyl |
| DCC | Dicyclohexylcarbodiimide |
| DMF | N,N-dimethylformamide |
| DMAP | 4-Dimethylaminopyridine |
| EDC | 1-(3-dimethylaminopropyl)-3-ethylcarbodi-imide hydrochloride |
| EI-MS | Electron ion-mass spectroscopy |
| Et | ethyl |
| eq. | equivalent(s) |
| FAB-MS | Fast atom bombardment-mass spectroscopy |
| HOBT, HOBt | Hydroxybenztriazole |
| HPLC | High pressure liquid chromatography |
| KHMDS | Potassium bis(trimethylsilyl)amide |
| LAH | Lithium aluminum hydride |
| LHMDS | Lithium bis(trimethylsilyl)amide |
| Me | methyl |
| MF | Molecular formula |
| MHz | Megahertz |
| MPLC | Medium pressure liquid chromatography |
| NMM | N-Methylmorpholine |
| NMR | Nuclear Magnetic Resonance |
| Ph | phenyl |
| Pr | propyl |
| prep. | prepared |
| TFA | Trifluoroacetic acid |
| THF | Tetrahydrofuran |
| TLC | Thin layer chromatography |
| TMS | Tetramethylsilane |

The compounds of the instant invention all have at least two asymmetric centers when both X and Y are groups other than hydrogen and are different from each other. Additional asymmetric centers may be present depending upon the nature of the various substituents on the molecule. Each such asymmetric center will independently produce two optical isomers and it is intended that all of the possible optical isomers and diastereomers in mixture and as pure or partially purified compounds are included within the ambit of this invention. In the case of the asymmetric carbon atom represented by an asterisk in Formula I, it has been found that compounds are more active as growth hormone secretagogues and, therefore preferred, in which the nitrogen substituent is above and the hydrogen atom is below the plane of the structure as represented in Formula II. An equivalent representation places $R^1$ and the N-substitutent in the plane of the structure with the C=O group above. This configuration corresponds to that present in a D-amino acid. In most cases, this is also designated an R-configuration, although this will vary according to the value of $R^1$ used in making R- or S- stereochemical assignments. In the case of the asymmetric center which bears the X and Y groups, in most cases, both R- and S- configurations are consistent with useful levels of growth hormone secretagogue activity. In addition configurations of many of the most preferred compounds of this invention are indicated. When the carbon atom in Formula I bearing an asterisk is of a defined and usually a D- configuration, two diastereomers result according to the absolute configuration at the carbon atom bearing the X and Y groups. These diastereomers are arbitrarily referred to as diastereomer 1 ($d_1$) and diastereomer 2 ($d_2$) in this invention and, if desired, their independent syntheses or chromatographic separations may be achieved as described herein. Their absolute stereochemistry may be determined by the x-ray crystallography of crystalline products or crystalline intermediates which are derivatized, if necessary, with a reagent containing an asymmetric center of known absolute configuration.

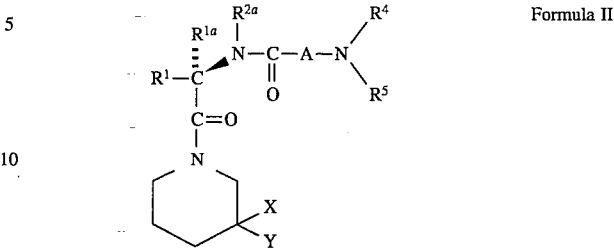

Formula II

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The preparation of compounds of Formula I of the present invention may be carried out in sequential or convergent synthetic routes. Syntheses detailing the preparation of the compounds of Formula I in a sequential manner are presented in the following reaction schemes.

The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The uses of protective groups for amine and carboxylic acid to facilitate the desired reaction and minimize undesired reactions are well documented. Conditions required to remove protecting groups which may be present and can be found in Greene, T, and Wuts, P. G. M., *Protective Groups in Organic Synthesis,* John Wiley & Sons, Inc., New York, N.Y. 1991. CBZ and BOG were used extensively in the synthesis, and their removal conditions are known to those skilled in the art. For example, removal of CBZ groups can be achieved by a number of methods known in the art; for example, catalytic hydrogenation with hydrogen in the presence of a nobel metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethylsulfide. Removal of BOC protecting groups is carried out in a solvent such as methylene chloride or methanol or ethyl acetate, with a strong acid, such as trifluoroacetic acid or hydrochloric acid or hydrogen chloride gas.

The protected amino acid derivatives 1 are, in many cases, commercially available, where the protecting group L is, for example, BOC or CBZ groups. Other protected amino acid derivatives 1 can be prepared by literature methods (Williams, R. M. *Synthesis of Optically Active α-Amino Acids,* Pergamon Press: Oxford, 1989). Many of the piperidines, pyrrolidines, and hexahydro-1H-azepines of Formula 2 are either commercially available or known in the literature and others can be prepared following literature methods described for analogous compounds. Some of these methods are illustrated in the subsequent schemes. The skills required

SCHEME 1

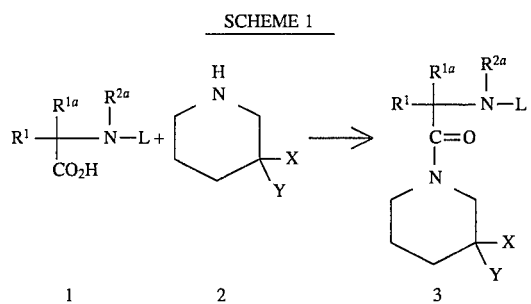

Intermediates of Formula 3 may be synthesized as described in Scheme 1. Coupling of amine of Formula 2, whose preparations are described later if they are not commercially available, to protected amino acids of Formula 1, wherein L is a suitable protecting group, is conveniently carried out under standard peptide coupling conditions.

SCHEME 2

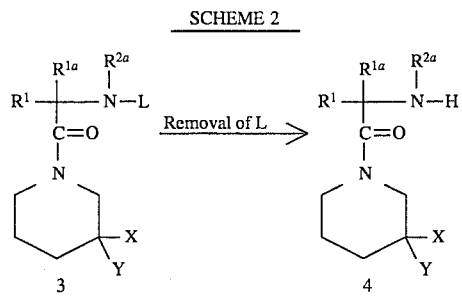

Conversion of 3 to intermediate 4 can be carried out as illustrated in Scheme 2 by removal of the protecting group L (CBZ, BOC, etc.)

amino acid 1, are either commercially available or can be synthesized by routine methods. Also if $R^4$ or $R^5$ is a hydrogen then the protected amino acids 6 are employed in the coupling reaction, wherein L is a protecting group as defined above. The removal of L in 7 to afford I, where $R^4$=H, can be carried out as noted above.

SCHEME 4

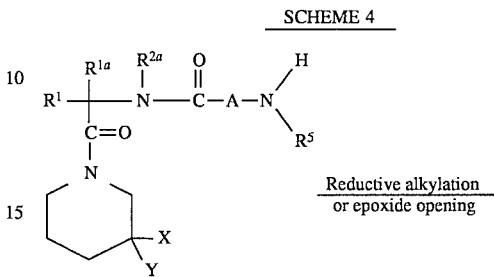

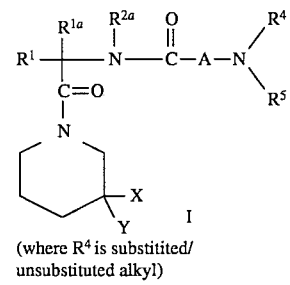

(where $R^4$ is substitited/ unsubstituted alkyl)

Compounds of Formula I wherein $R^4$ and/or $R^5$ is a hydrogen may be further elaborated to new Compounds I (with side chains $R^4$=$R^2$ or $CH_2$—CH(OH)—$CH_2$X, wherein X=H or OH) which are substituted on the amino group as depicted in Scheme 4. Reductive alkylation of I with an aldehyde is carried out under conditions known in the art; for example, by catalytic hydrogenation with hydrogen in the presence of platinum, palladium, or nickel catalysts or with chemical reducing agents such as sodium

SCHEME 3

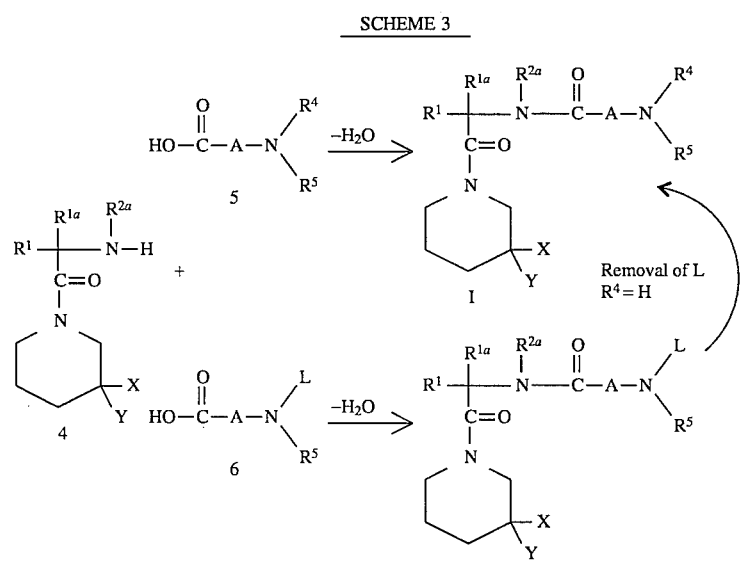

Intermediates of Formula 5, wherein A is —$(CH_2)_x$—$C(R^7)(R^{7a})$—$(CH_2)_y$,— may be coupled to intermediates of Formula 4 to afford compounds of Formula I under standard peptide coupling reaction conditions. The amino acids 5, as cyanoborohydride in a protic solvent such as methanol or ethanol in the present of catalytic amount of acid. Alternatively, a similar transformation can be accomplished via an epoxide opening reaction.

SCHEME 5

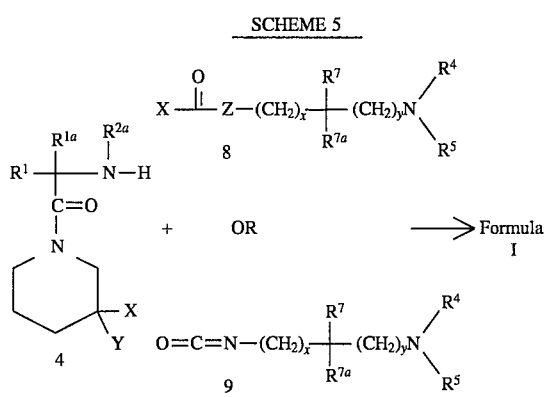

Compounds of Formula I, wherein A is Z—(CH$_2$)$_x$—C(R$^7$)(R$^{7a}$)—(CH$_2$)$_y$, and Z is N—R$^{6a}$ or O may be prepared as shown in Scheme 5 by reacting 4 with reagents 8, wherein X is a good leaving group such as Cl, Br, I, or imidazole. Alternatively, 4 may be reacted with an isocyanate of Formula 9 in an inert solvent such as 1,2-dichloroethane to provide compounds of Formula I where Z is NH.

SCHEME 6

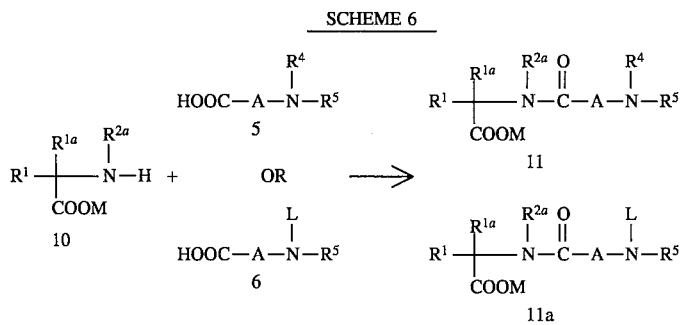

The compounds of general Formula I of the present invention may also be prepared in a convergent manner as described in reaction Schemes 6, 7 and 8.

The carboxylic acid protected amino acid derivatives 10 are, in many cases, commercially available where M=methyl, ethyl, or benzyl esters. Other ester protected amino acids can be prepared by classical methods familiar to those skilled in the art. Some of these methods include the reaction of the amino acid with an alcohol in the presence of an acid such as hydrochloric acid or p-toluenesulfonic acid and azeotropic removal of water. Other reactions includes the reaction of a protected amino acid with a diazoalkane, or with an alcohol and an acid activating agent such as EDC, DCC in the presence of a catalyst such as DMAP and removal of the protecting group L.

Intermediates of Formula 11 or 11a, may be prepared as shown in Scheme 6 by coupling of amino acid ester 10 to amino acids of Formula 5 or 6. When a urea or carbamate linkage is present in 11 or 11a, it can be introduced as illustrated in Scheme 5.

SCHEME 7

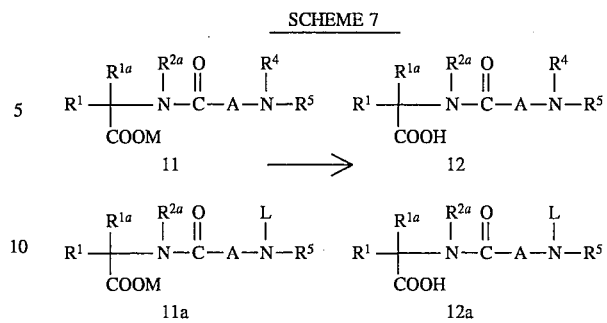

Conversion of the ester 11 or 11a to intermediate acids 12 or 12a may be achieved by a number of methods known in the art as described in Scheme 7; for example, methyl and ethyl esters can be hydrolyzed with lithium hydroxide in a protic solvent like aqueous methanol. In addition, removal of benzyl group can be accomplished by a number of reductive methods including hydrogenation in the presence of palladium catalyst in a protic solvent such as methanol. An allyl ester can be cleaved with tetrakis-triphenylphosphine palladium catalyst in the presence of 2-ethylhexanoic acid in a variety of solvents including ethyl acetate and dichloromethane (see *J. Org. Chem.*, 42, 587 (1982)).

SCHEME 8

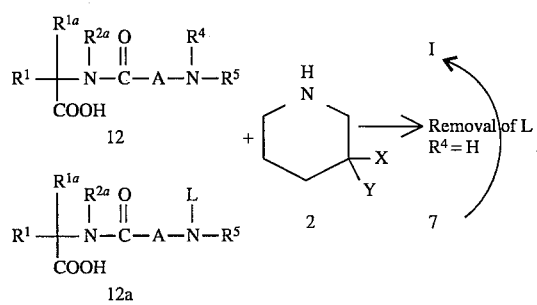

Acid 12 or 12a may then be elaborated to I or to I bearing protecting group L (Compound I) as described in Scheme 8. Coupling of piperidines of Formula 2 to acids of Formula 12 or 12a, is conveniently carried out under the standard peptide coupling reaction conditions. Transformation of 7 to I is achieved by removal of the protecting group L. When R$^4$ and/or R$^5$ is H, substituted alkyl groups may be optionally added to the nitrogen atom as described in Scheme 4.

SCHEME 9

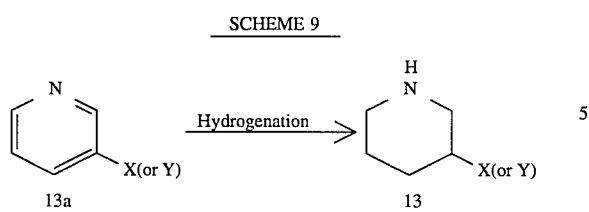

3-Monosubstituted piperidines of formula 13 can be prepared by the reduction of pyridine derivatives or their salts by hydrogenation in a suitable organic solvent such as water, acetic acid, alcohol, e.g. ethanol, or their mixture, in the presence of a noble metal catalyst such as platinum or an oxide thereof on a support such as activated carbon, and conveniently at room temperature and atmospheric pressure or under elevated temperature and pressure. 3-Monosubstituted piperidines can also be prepared by modification of the X or Y moiety of the existing 3-monosubstituted piperidines.

SCHEME 10

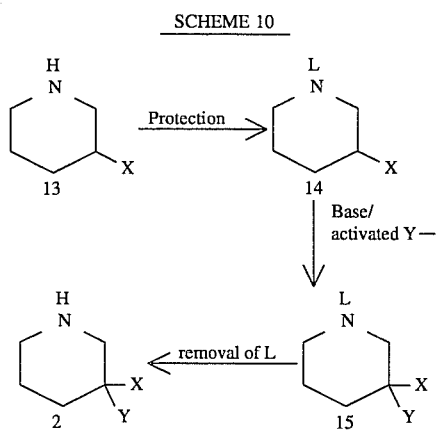

Illustrated in Scheme 10 is a general way to prepare disubstituted piperidines. Compounds of Formula 13 wherein X is an electron withdrawing group such as —CN, —CO$_2$R$^2$, where R$^2$ is alkyl, aryl, and (C$_1$–C$_4$alkyl)aryl are known compounds or may be prepared by methods analogous to those used for the preparation of such known compounds. The secondary amine of compounds of Formula 13 may be first protected by a protecting group L such as BOC and CBZ using the conventional techniques. Introduction of the Y substitution can be achieved by first reacting compounds of Formula 14 with a strong base such as lithium bis(trimethylsilyl)amide, lithium diisopropylamide following by addition of alkylating or acylating reagents such as alkyl halides, aryl alkyl halides, acyl halides, and haloformates in a inert solvent such as THF at temperatures from −100° C. to room temperature. Thio derivatives where the sulfur is attached directly to an alkyl or an aryl group can be prepared similarly by reacting with a disulfide. The halides used in these reactions are either commercially available or known compounds in the literature or may be prepared by methods analogous to those used for the preparation of known compounds. The protecting group L in compounds of formula 15 may be removed with conventional chemistry to give compounds of Formula 2.

SCHEME 11

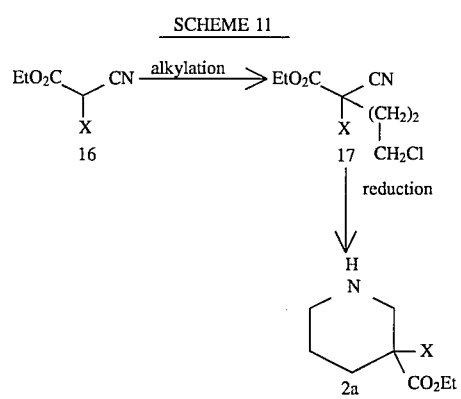

Alternative ways of preparing compounds of Formula 2 include construction of the ring itself (Jacoby, R. L. et al, *J. Med. Chem.*, 17, 453–455, (1974)). Alkylation of the cyanoacetates of general formula 16, which are commercially available or may be prepared from literature procedures, with alkyl dihalides such as 1-bromo-2-chloroethane or 1-bromo-3-chloropropane yields the chloride 17. Reduction of the nitriles 17 by borane or by hydrogenation using Raney Ni as a catalyst gives the corresponding primary amines, which upon refluxing in ethanol give compounds of Formula 2a.

SCHEME 12

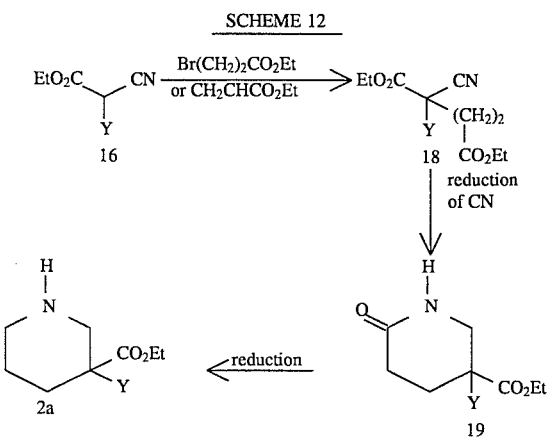

Alternatively, the cyanoacetates of general formula 16 may be alkylated with an ethoxycarbonylalkyl bromide or reacted with ethyl acrylate to give compounds of Formula 18. Reduction of the nitriles 18 by borane or by hydrogenation using Raney Ni as a catalyst gives the corresponding primary amines, which upon refluxing in ethanol gives lactam 19. Reduction of the lactam 19 by borane gives compounds of Formula 2a.

SCHEME 13

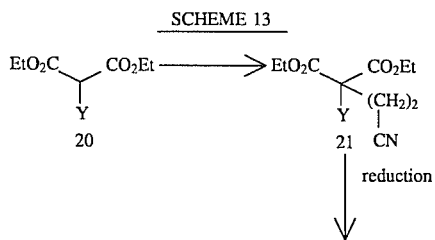

21
-continued
SCHEME 13

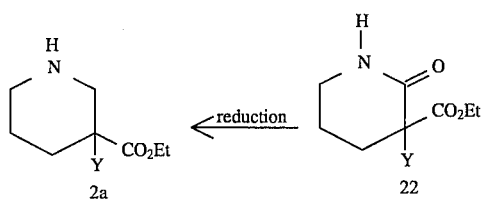

Alternatively, a malonate of general formula 20 may be alkylated with cyanoalkyl bromide or can be reacted with acrylonitrile to form compounds of formula 21. Reduction of the nitriles 21 by borane or by hydrogenation using Raney Ni as a catalyst gives the corresponding primary amines, which upon refluxing in ethanol gives lactam 22. Reduction of the lactam 22 by borane gives compounds of formula 2a.

SCHEME 14

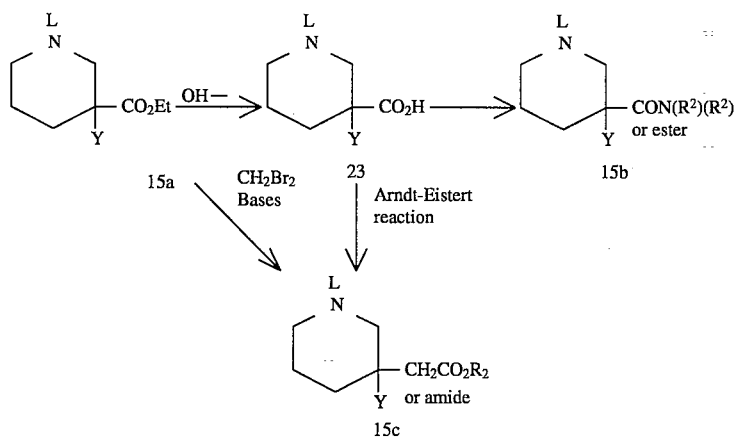

The X, Y functionalities in compounds of general structure may be further elaborated to groups not accessible by direct alkylation. For example in Compound 15 when X=CO$_2$Et the ester (provided that this is the only ester group in the molecule) can be saponified to the carboxylic acid, which can be further derivatized to amides or other esters. The carboxylic acid can be converted into its next higher homologue, or to a derivative of the homologous acid, such as amide or ester by an Arndt-Eistert reaction. Alternatively, the ester can be directly homologated by the protocol using ynolate anions described by C. J. Kowalski and R. E. Reddy in *J. Org. Chem.*, 57, 7194–7208 (1992). The resulting acid and/or ester may be converted to the next higher homologue, and so on and so forth. The protecting group L may be removed through conventional chemistry.

SCHEME 15

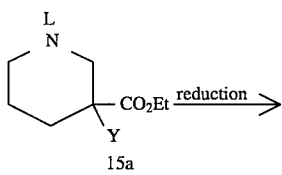

22
-continued
SCHEME 15

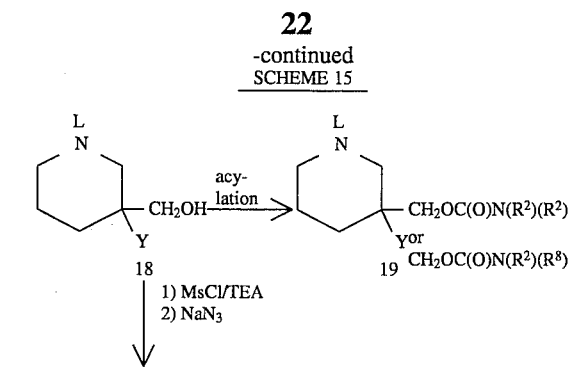

-continued
SCHEME 15

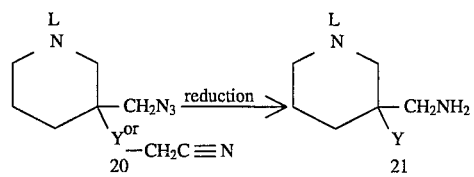

The ester in 15a may be reduced to an alcohol 18 in a suitable solvent such as THF or ether with a reducing agent such as DIBAL-H and conveniently carried out at temperatures from −100° C. to 0° C. The alcohol may be convened to Compound 19 in a suitable solvent such as dichloromethane using the corresponding isocyanate or with a reagent such as T-C(O)N(R$^2$)(R$^8$) where T is leaving group like p-nitrophenol. The hydroxy group in 18 may also be convened to a good leaving group such as mesylate and displaced by a nucleophile such as cyanide or an azide. Reduction of the azide in compounds of Formula 20 to an amine 21 can be achieved by hydrogenation in the presence of a noble metal such as palladium or its oxide or Raney nickel in a protic solvent such as ethanol. The nitrile can be reduced to afford the homologous amine. The amine of Formula 21 may be further elaborated to amides, ureas sulfonamides as defined by X through conventional chemistry. The protecting group L may be removed through conventional chemistry.

SCHEME 16

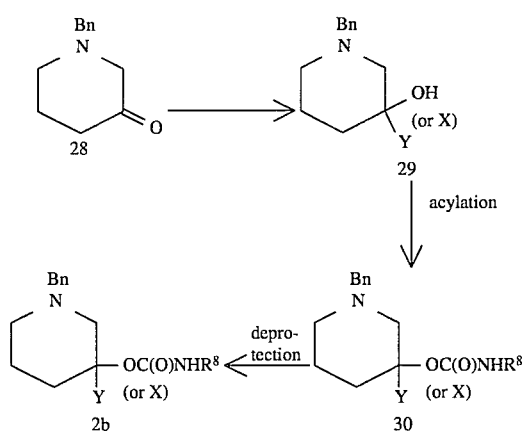

In cases where oxygen is directly attached to the ring, a convenient method involves the addition reaction by an activated form of an alkyl, aryl, alkylaryl group, such as lithium reagent, Grignard reagents, and the like with a ketone of general formula 28, which is commercially available. Further derivatization of the resulting hydroxy group by reaction with isocyanates or with T-C(O)N(R$^8$)(R$^2$) where T is leaving group like p-nitrophenol or N-hydroxysuccinimide and the like gives compounds as defined by Y or X through conventional chemistry. Removal of the benzyl protective group may be carried out under the usual conditions to give compounds of general formula 2b. Shown in Scheme 16 is a general example of acylations.

SCHEME 17

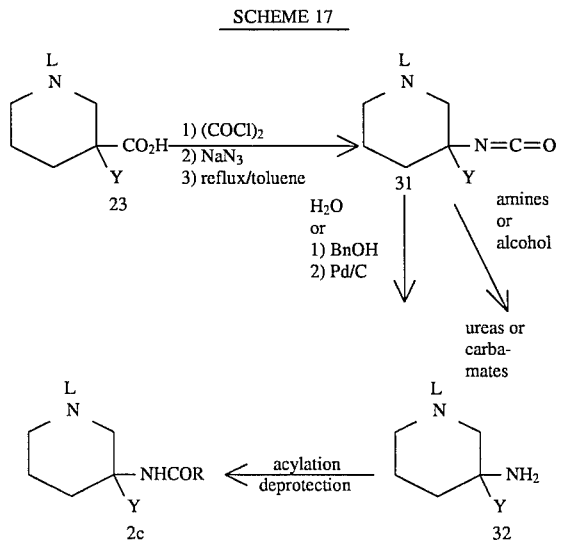

In cases where a nitrogen-substituted group is directly attached to the ring, a convenient method is to use the Curtius rearrangement on the acid 23 to afford the isocyanate 31. Addition of amines or alcohols give ureas or carbamates respectively which can be deprotected to remove L to give special cases of compounds of formula 2. Conversion of the isocyanate to amine by hydrolysis gives compound 32. Further derivatization of the resulting amine group by acylation, sulfonylation, alkylation, and the like to give compounds as defined by Y or X can be done through conventional chemistry. Removal of the protective group L may be carried out under the usual conditions to give compounds of general formula 2c. Shown in Scheme 17 is a general example of acylations.

SCHEME 18

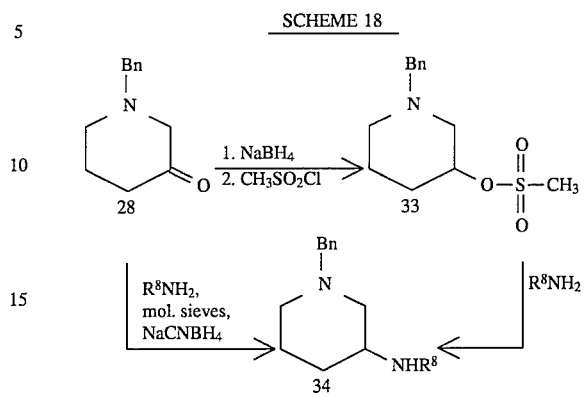

Compounds of formula 34 may also be prepared from N-protected 3-piperidones by reductive alkylation of an amine using reducing agents such as sodium cyanoborohydride optimally in the presence of a means of promoting Schiff base formation such as with molecular sieves. Furthermore, the N-protected 3-piperidone can be reduced to the alcohol as illustrated in Scheme 18, acylated with a good leaving group like mesylate which in turn is displaced by R$^8$NH$_2$ to afford compound 34.

SCHEME 19

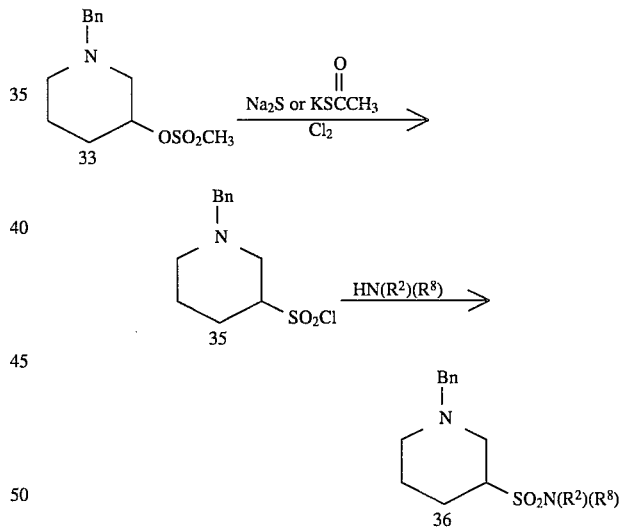

Intermediates of formula 36 may be prepared from mesylate 33 by displacing this group with a sulfide or with potassium thioacetate followed by oxidation to the sulfonyl chloride using Cl$_2$. Displacement of the chloride with HN(R$^2$)(R$^8$) affords the corresponding sulfonamide 36. If R$^2$ is hydrogen the sulfonamide may be further alkylated with a strong base such as NaH in DMF followed by an equivalent of an alkyl or arylalkyl halide. Alternatively, the compound 33 may be reacted with sodium sulfite to afford a sulfonic acid that can be reacted with oxalyl chloride or thionyl chloride to give compound 35 which is converted to 36 as outlined in Scheme 19.

SCHEME 20

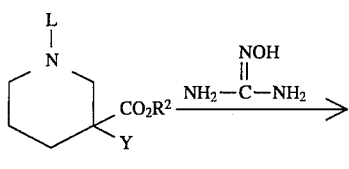

15a

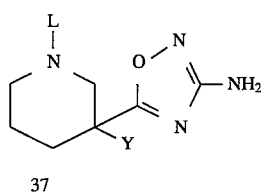

37

The introduction of hererocycles in the piperidine 3-position from cyano, iminoether, ester, amide and hydroxyamidine substituents in that position is done by methods known in the art. As illustrated in Scheme 20 a 3-amino-1,2,4-oxadiazol-5-yl is synthesized by reacting an ester with hydroxyguanidine in a protic solvent such as ethanol int he presence of sodium ethoxide at reflux. 5-Alkyl-1,2,4-oxadiazol-5-yls are prepared by acylating a protected piperidine 3-hydroxyamidine with an acid chloride in a solvent like pyridine at elevated temperatures.

Compounds of the general formula 2 prepared in this manner are racemic when X and Y are not identical. Resolution of the two enatiomers can be conveniently achieved by classical crystallization methods by using a chiral acid such as L- or D-tartaric acid, (+) or (−)-10-camphorsulfonic acid in a suitable solvent such as acetone, water, alcohol, ether, acetate or their mixture. Alternatively, the racemic amine can be reacted with a chiral auxiliary such as (R) or (S)—O—acetylmandelic acid followed by chromatographic separation of the two diastereomers, and removal of the chiral auxiliary by hydrolysis. Alternatively asymmetric alkylation can also be utilized for the synthesis of optically active intermediate by introducing a removable chiral auxiliary in X or in place of L with subsequent chromatographic separation of diastereomers.

In cases where a sulfide is present in the molecule, it may be oxidized to a sulfoxide or to a sulfone with oxidizing agents such as sodium periodate, m-chloroperbenzoic acid or Oxone® in an solvent such as dichloromethane, alcohol or water or their mixtures.

The compounds of the present invention may also be prepared from a variety of substituted natural and unnatural amino acids of formulas 46. The preparation of many of these acids is described in U.S. Pat. No. 5,206,237. The preparation of these intermediates in racemic form is accomplished by classical methods familiar to those skilled in the art (Williams, R. M. "Synthesis of Optically Active α-Amino Acids" Pergamon Press: Oxford, 1989; Vol. 7). Several methods exist to resolve (DL)-

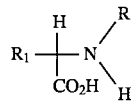

38 amino acids. One of the common methods is to resolve amino or carboxyl protected intermediates by crystallization of salts derived from optically active acids or amines. Alternatively, the amino group of carboxyl protected intermediates may be coupled to optically active acids by using chemistry described earlier. Separation of the individual diastereomers either by chromatographic techniques or by crystallization followed by hydrolysis of the chiral amide furnishes resolved amino acids. Similarly, amino protected intermediates may be converted to a mixture of chiral diastereomeric esters and amides. Separation of the mixture using methods described above and hydrolysis of the individual diastereomers provides (D) and (L) amino acids. Finally, an enzymatic method to resolve N-acetyl derivatives of (DL)-amino acids has been reported by Whitesides and coworkers in J. Am. Chem. Soc. 1989, 111, 6354–6364.

When it is desirable to synthesize these intermediates in optically pure form, established methods include: (1) asymmetric electrophilic amination of chiral enolates (J. Am. Chem. Soc. 1986, 108, 6394–6395, 6395–6397, and 6397–6399), (2) asymmetric nucleophilic amination of optically active carbonyl derivatives, (J. Am. Chem. Soc. 1992, 114, 1906; Tetrahedron Lett. 1987, 28, 32), (3) diastereoselective alkylation of chiral glycine enolate synthons (J. Am. Chem. Soc. 1991, 113, 9276; J. Org. Chem. 1989, 54, 3916), (4) diastereoselective nucleophilic addition to a chiral electrophilic glycinate synthon (J. Am. Chem. Soc. 1986, 108, 1103), (5) asymmetric hydrogenation of prochiral dehydroamino acid derivatives ("Asymmetric Synthesis, Chiral Catalysis; Morrison, J. D., Ed; Academic Press: Orlando, F.L., 1985; Vol 5), and (6) enzymatic syntheses (Angew. Chem. Int. Ed. Engl. 1978, 17, 176).

SCHEME 21

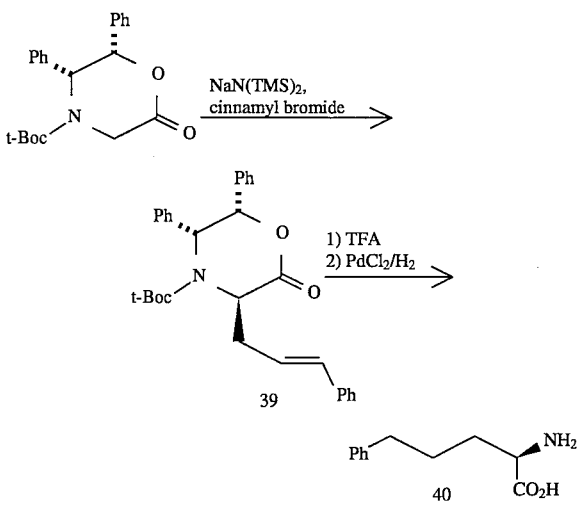

For example, alkylation of the enolate of diphenyloxazinone 38a (J. Am. Chem. Soc. 1991, 113, 9276) with cinnamyl bromide in the presence of sodium bis(trimethylsilyl)amide proceeds smoothly to afford which is converted into the desired (D)-2-amino-5-phenylpentanoic acid 40 by removing the N-t-butyloxycarbonyl group with trifluoroacetic acid and hydrogenation over a PdCl₂ catalyst (Scheme 21).

SCHEME 22

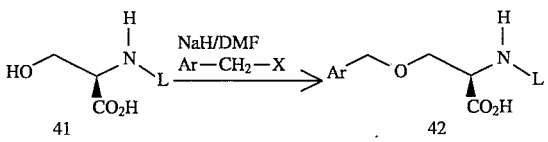

Intermediates of formula 42 which are O-benzyl-(D)-serine derivatives 42 are conveniently prepared from suitably substituted benzyl halides and N-protected-(D)-serine 41. The protecting group L is conveniently a BOC or a CBZ group. Benzylation of 41 can be achieved by a number of methods well known in the literature including deprotonation with two equivalents of sodium hydride in an inert solvent such as DMF followed by treatment with one equivalent of a variety of benzyl halides (Synthesis 1989, 36) as shown in Scheme 22.

The O-alkyl-(D)-serine derivatives may also be prepared using an alkylation protocol. Other methods that could be utilized to prepare (D)-serine derivatives of formula 42 include the acid catalyzed benzylation of carboxyl protected intermediates derived from 41 with reagents of formula Ar—$CH_2OC(=NH)CCl_3$ (O. Yonemitsu et al., Chem. Pharm. Bull. 1988, 36, 4244). Alternatively, alkylation of the chiral gylcine enolates (J. Am. Chem. Soc. 1991, 113, 9276; J. Org. Chem. 1989, 54, 3916) with $ArCH_2OCH_2X$ where X is a leaving group affords 43. In addition D,L-O-aryl(alkyl)serines may be prepared and resolved by methods described above.

It is noted that in some cases the order of carrying out the foregoing reaction schemes may be varied to facilitate the reaction or to avoid unwanted reaction products.

The utility of the compounds of the present invention as growth hormone secretagogues may be demonstrated by methodology known in the art, such as an assay described by Smith, et al., Science, 260, 1640–1643 (1993) (see text of FIG. 2 therein). In particular, the intrinsic growth horomone secretagogue activities of the compounds of the present invention may be demonstrated in this assay. The compounds of the following examples have activity in the aforementioned assay in the range of 0.1 nm to 5 μm.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release and that the growth hormone releasing factor (GRF) stimulates its release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the catabolic side effects or with other pharmaceutically active materials wherein the combination enhances efficacy and minimizes side effects.

Growth promoting and anabolic agents include, but are not limited to, TRH, diethylstilbesterol, estrogens, β-agonists, theophylline, anabolic steroids, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox. or peptides disclosed in U.S. Pat. No. 4,411,890.

A still further use of the growth hormone secretagogues of this invention is in combination with other growth hormone secretagogues such as the growth hormone releasing peptides GHRP-6, GHRP-1 as described in U.S. Pat. Nos. 4,411,890 and publications WO 89/07110, WO 89/07111 and B-HT920 as well as hexarelin and GHRP-2 as described in WO 93/04081 or growth hormone releasing hormone (GHRH, also designated GRF) and its analogs or growth hormone and its analogs or somatomedins including IGF-1 and IGF-2 or α-adrenergic agonists such as clonidine or serotonin 5HTID agonists such as sumitriptan or agents which inhibit somatostatin or its release such as physostigmine and pyridostigmine. For example, a compound of the present invention may be used in combination with IGF-1 for the treatment or prevention of obesity. In addition, a compound of this invention may be employed in conjunction with retinoic acid to improve the condition of musculature and skin that results from intrinsic aging.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses may be summarized as follows: treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia, treatment of peripheral neuropathies; replacement of growth hormone in stressed patients; treatment of osteochondrody-splasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development and preventtion of the age-related decline of thymic function; adjunctive therapy for patients on chronic hemodialysis; treatment of immunosuppressed patients and to enhance antibody response following vaccination; increasing the total lymphocyte count of a human, in particular, increasing the $T_4/T_8$-cell ratio in a human with a depressed $T_4/T_8$-cell ratio resulting, for example, from infection, such as bacterial or viral infection, especially infection with the human immunodeficiency virus; treatment of syndromes manifested by non-restorative sleep and musculoskeletal pain, including fibromyalgia syndrome or chronic fatigue syndrome; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock. Likewise, the instant compounds are useful in a method of treatment of diseases or conditions which are benefited by the anabolic effects of enhanced growth hormone levels that comprises the administration of an instant compound.

In particular, the instant compounds are useful in the prevention or treatment of a condition selected from the group consisting of: osteoporosis; catabolic illness; immune deficiency, including that in individuals with a depressed $T_4/T_8$ cell ratio; hip fracture; musculoskeletal impairment in the elderly; growth hormone deficiency in adults or in children; obesity; cachexia and protein loss due to chronic illness such as AIDS or cancer; and treating patients recovering from major surgery, wounds or burns, in a patient in need thereof.

In addition, the instant compounds may be useful in the treatment of illnesses induced or facilitated by corticotropin releasing factor or stress- and anxiety-related disorders, including stress-induced depression and headache, abdominal bowel syndrome, immune suppression, HIV infections, Alzheimer's disease, gastrointestinal disease, anorexia nervosa, hemorrhagic stress, drug and alcohol withdrawal symptoms, drug addiction, and fertility problems.

It will be known to those skilled in the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N.A.T., "Role of Bisphosphonates in Metabolic Bone Diseases" *Trends in Endocrinol. Metab.*, 4, 19–25 (1993). Bisphosphonates with these utilities include alendronate, tiludronate, dimethyl-APD, risedronate, etidronate, YM-175, clodronate, pamidronate, and B M-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

In the case of alendronate daily oral dosage levels of 0.1 mg to 50 mg are combined for effective osteoporosis therapy with 0.01 mg/kg to 20 mg/kg of the growth hormone secretagogues of this invention.

Osteoporosis and other bone disorders may also be treated with compounds of this invention in combination with calcitonin, estrogens, raloxifene and calcium supplements such as calcium citrate.

Anabolic effects especially in the treatment of geriatric male patients are obtained with compounds of this invention in combination with anabolic steroids such as oxymetholone, methyltesterone, fluoxymesterone and stanozolol.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.000 g to 10 mg/kg. of body weight daily are administered to patients and animals, e.g., mammals, to obtain effective release of growth hormone.

The following examples are provided for the purpose of further illustration only and are not intended to be limitations on the disclosed invention.

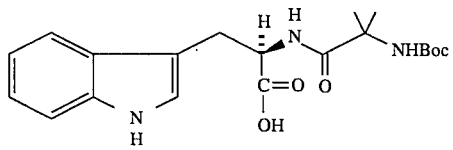

Step A:

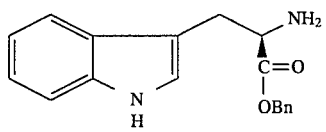

To a solution of the commercially available N-t-BOC-D-tryptophan (25.0 g, 82.2 mmol), benzyl alcohol (10.2 mL, 98.6 mmol), and DMAP (100 mg) in dichloromethane (200 mL) at 0° C., was added EDC (17.4 g, 90.4 mmol) in several portions over a one hour period. The reaction mixture was stirred at room temperature for six hours and was poured into water (200 mL), and the organic layer was separated. The organic solution was washed with a mixture of brine and 3N hydrochloric acid, dried over anhydrous magnesium sulfate, filtered and concentrated to give a thick oil, which solidified upon standing.

To a solution of this oil in 30 mL of dichloromethane was added 20 mL of TFA and stirred for 1h. The reaction mixture was concentrated, neutralized carefully with saturated aqueous sodium bicarbonate solution, and extracted with dichloromethane (2×100 mL). The combined organic solution was washed with brine (100 mL), passed through a short column of silica gel eluting with 5–10% methanol in dichloromethane to give 23.2 g of the amine as an oil after evaporation.

Step B:

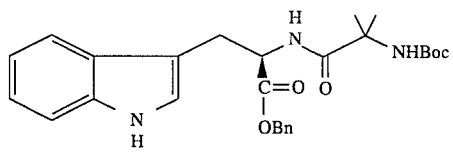

To a solution of the above product, HOBT (10.6 g, 78.8 mmol) and N-BOC-α-methyl alanine (19 g, 94.5 mmol) in 200 mL of dichloromethane, was added EDC (19.5 g, 0.102 mol) in several portions at 0° C. After 5 minutes, the clear reaction mixture became milky. After stirring at room temperature overnight, the reaction mixture was poured into 200 mL of water and the organic layer was separated. The organic solution was washed with brine, and with a brine and saturated sodium bicarbonate solution, dried over anhydrous magnesium sulfate, filtered and concentrated to give a thick oil, which was purified by flash chromatography eluting with 10–40% ethyl acetate in hexane to give the desired material (28.7 g).

$^1$H NMR (CDCl$_3$, 200 MHz) δ8.48 (br.s, 1H), 7.54 (br.d, 1H), 7.38–7.23 (m, 3H), 7.19 (br.d, 2H), 7.15–7.00 (m, 1H), 6.90 (d, 1H), 6.86 (d, 1H), 5.06 (br.s, 2H), 4.95 (ddd, 1H), 3.30 (2dd, 2H), 1.40 (s, 15H)

Step C:

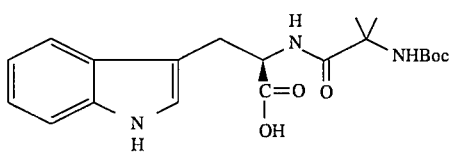

A solution of the material from Step B (28.7 g) in 200 mL of ethanol was stirred at RT under a H$_2$ balloon for 20 minutes in the presence of 10% palladium on carbon (2 g). The catalyst was filtered off through a pad of celite and washed with ethyl acetate. The filtrate was concentrated to give the acid as a slightly pink foam (23.3 g).

$^1$H NMR (CD$_3$OD, 400 MHz) δ7.56 (d, J=8 Hz, 1H), 7.31 (dd, J=1,8 Hz, 1H), 7.09 (s, 1H), 7.07 (dt, J=1,7 Hz, 1H), 6.98 (dt, J=1,7 Hz, 1H), 4.69 (t, J=6 Hz, 1H), 3.34–3.23 (m, 2H), 1.35 (s, 3H), 1.34 (s, 9H) 1.29 (s, 3H). FAB-MS calc. for C$_{20}$H$_{27}$N$_3$O$_5$: 389; Found 390 (M+H), 290 (M+H–100 (BOG))

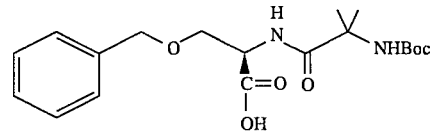

Following the procedures for the preparation of Intermediate using N-t-Boc-O-Benzyl-D-serine in the place of N-t-BOC-D-tryptophan gave Intermediate 2. FAB-MS calc. for C$_{19}$H$_{28}$N$_2$O$_6$: 380; Found 381 (M+H), 325 (M+H-56 (t-Bu)), 281 (M+H-100 (BOC)).

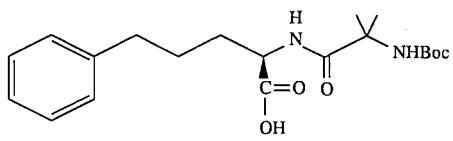

Step A:

(DL)-N-Acetyl-2-amino-5-phenylpentanoic acid

To a solution of sodium (2.3 g, 0.1 mol) in ethanol (60 mL) under nitrogen at room temperature, was added diethyl acetamidomalonate. The mixture was stirred at room temperature for one hour, and then 1-bromo-3-phenylpropane was added dropwisely. After the addition, the mixture was stirred at room temperature for two hours, then refluxed overnight. It was cooled to room temperature and partitioned between water and ethyl acetate. The organic layer was washed with sodium bicarbonate in water, dried over MgSO4 and evaporated to give an intermediate (32.5 g, 97%).

¹H NMR (CDCl₃, 400 MHz) 7.26–7.10 (m, 5H); 6.75 (br. s, 1H); 4.19 (q, J=7 Hz, 4H); 2.58 (t, J=7.9 Hz, 2H); 2.39–2.35 (m, 2H); 2.00 (s, 3H); 1.43–1.39 (m, 2H); 1.20 (t, J=7 Hz, 6H).

The product above was suspended in 190 mL of 2.5N NaOH in water and refluxed for two hours. The mixture was cooled to 0° C., and it was carefully neutralized with 6N HCl to pH2. The precipitate was collected using a glass sinter funnel and washed with a small amount of cold water and air dried. The solid was then suspended in 300 mL of water and refluxed for four hours. The solution was cooled and acidified to pH1 and the solid was collected by filtration (15.3 g, 67%).

¹H NMR (CD3OD, 400 MHz) 7.26–7.12 (m, 5H); 4.90–4.37 (m, 1H); 2.65–2.60 (m, 2H); 1.97 (s, 3H); 1.87–1.82 (m, 1H); 1.73–1.65 (m, 3H).

Step B:

(D)-N-Acetyl-2-amino-5-phenylpentanoic acid

The racemic intermediate from the previous step (10 g, 42.5 mmol) and CoCl3-6H₂O were dissolved in 21 ml of 2N KOH and 200 mL of water at 40° C., and the pH of the solution was adjusted to 8 by the addition of the several drops of 2N KOH. Then acylase I (Aspergillus sp, 0.5 μ/rag, from Sigma; 0.9 g) was added with vigorous stirring. The reaction mixture was stirred for one day at 40° C. and the pH was kept at 8 by the addition of a few drops of KOH. The solid which formed was filtered off. The tiltrate was acidified by 3N HCl to pH2, and was extracted with ethyl acetate (200 mL×4). The organic extracts were combined and evaporated to give a white solid (4.64 g, 46%) ¹H NMR (CD3OD, 400 MHz) 7.26–7.12 (m, 5H); 4.90–4.37 (m, 1H); 2.65–2.60 (m, 2H); 1.97 (s, 3H); 1.87–1.82 (m, 1H); 1.73–1.65 (m, 3H).

Step C:

(D)-N-t-Boc-2-amino-5-phenylpentanoic acid

The intermediate from step B (4.2 g, 17.8 mmol) was suspended in 2N HCl (100 mL) and refluxed for two hours. The reaction mixture was evaporated in vacuo to remove water and hydrochloric acid to yield a white solid. To a solution of this solid in 50 mL of water, was added 3N NaOH until the pH 11, then di-t-butyl dicarbonate (4.66 g, 21.4 mmol) was added with vigorous stirring. After four hours, the reaction mixture was acidified to pH2 with 3N HCl and it was extracted with ethyl acetate (100 mL×3 ). The organic extracts were combined and evaporated to give a white solid (6.56 g, crude) which was used without purification. ¹H NMR (CD3OD, 400 MHz) 7.26–7.12 (m, 5H); 4.11–4.08 (m, 1H); 2.65–2.60 (m, 2H); 1.83–1.62 (m, 4H); 1.43 (s, 9H).

Step D:

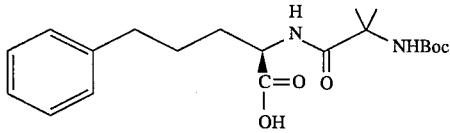

Following the procedures for the preparation of Intermediate 1 using (D)-N-t-Boc-2-amino-5-phenylpentanoic acid in the place of N-t-BOC-D-tryptophan gave Intermediate 3.

¹H NMR (CDCl₃, 400 MHz) 7.24–7.20 (m, 2H), 7.15–7.04 (m, 3H), 4.60–4.55 (m, 1H), 2.62–2.55 (m, 2H), 2.00–1.86 (m, 1H), 1.78–1.60 (m, 3H), 1.50 (s, 6H), 1.30 (s, 9H).

EXAMPLE 1

N'-Benzyl-N'-phenylsulfonyl-3-amino-piperidine hydrochloride

Step A:

N-(tert-Butoxycarbonyl)-3-piperidinol

To a solution of 3-piperidinol (2.51 g; 18.2 mmol) in 10% Na₂CO₃ (66 ml) and dioxane (27 ml), cooled to 0° C., is added di-tert -butyl dicarbonate (3.57 g; 17.1 mmol) portionwise. After the addition, the reaction mixture was stirred for an additional two hours at room temperature. The aqueous phase was extracted with EtOAc (5×100 ml). The combined organic extracts were then washed with 10% aqueous citric acid, water, saturated aqueous NaCl, dried (MgSO₄), filtered, and evaporated. The compound was dried in vacuo to afford 2.93 g of the title compound which was used in the next step without further purification.

¹H-NMR (300 MHz, CD₃OD, ppm): δ1.03–1.53 (m, 11H), 1.54–1.79 (m, 1H), 1.80–1.95 (m, 1H), 2.53–3.09 (m, 2H), 3.4–3.53 (m, 1H), 3.55–3.72 (m, 1H), 3.73–3.90 (dd, 1H).

Step B:

N:(tert-Butoxycarbonyl)piperidin-3-one

To a cooled (−65° C.) solution of DMSO (1.42 ml; 20 mmol) in CH₂Cl₂ (30 ml) was added oxalyl chloride (0.87 ml; 10 mmol). The resulting suspension was stirred for an additional 15 minutes at −65° C., whereupon the product of Step A (2.17 g; 10 mmol) dissolved in 5 ml of CH₂Cl₂ was added portionwise and the reaction was stirred for an additional 15 minutes at that temperature. Triethylamine (5.56 ml; 40 mmol) was then added dropwise, and the solution was allowed to warm to room temperature, whereupon the reaction was stirred for an additional 1.5 hours. The reaction was quenched with H₂O and extracted several times with EtOAc. The combined organic phase was washed with 10% aqueous citric acid, H₂O, saturated aqueous NaCl, dried (MgSO₄), filtered and evaporated. The residue was purified on a silica gel flash chromatography column eluted with 25% EtOAc-hexanes. The fractions containing pure material were combined and concentrated in vacuo to afford 1.87 g of the title compound as a yellow oil.

¹H-NMR (400 MHz, CD₃OD, ppm): δ1.38–1.48 (s, 9H), 1.52–1.72 (m, 1H), 1.90–2.00 (p, 1H), 2.40–2.50 (t, 1H), 2.95–3.15 (m, 1H), 3.45–3.80 (m, 3H), 3.90–4.00 (s, 1H).

Step C.

N-(tert-Butoxycarbonyl)-N-benzyl-3-aminopiperidine

To a solution of the title compound in Step B (500 mg; 2.5 mmol) in MeOH (7 ml) consisting of HOAc (425 μl), benzylamine (273 μl; 2.5 mmol), and 4 A° powdered sieves, was added NaCNBH₃ (319 mg; 5.0 mmol) at room temperature. The reaction was stirred at room temperature for two hours, whereupon it was quenched with H₂O and extracted with EtOAc (2×200 ml). The combined organic extracts were washed with 1N aqueous NaOH, H₂O, saturated aqueous NaCl, dried (MgSO₄), filtered and evaporated. The residue was purified by silica gel radial chromatography eluted with CH₂Cl₂ followed by CH₂Cl₂-MeOH (20:1). The fractions containing pure material were combined and concentrated in vacuo to afford 601 mg of the title compound as a yellow oil. The material was used as is in the next step.

Step D:

N-(tert-Butoxycarbonyl)-N-benzyl-N'-phenylsulfonyl-3-aminopiperidine

To a solution of the title compound in Step C (601 mg; 2.07 mmol) in $CH_2Cl_2$ (2 ml) and N-methylmorpholine (227 μl; 2.07 mmol), cooled to 0° C., was added phenylsulphonylchloride (396 μl; 3.1 mmol), and the reaction was allowed to stir at room temperature for three hours. The reaction was quenched with $H_2O$ and extracted with EtOAc. The organic phase was washed with $H_2O$, saturated aqueous NaCl, dried ($MgSO_4$), filtered and evaporated. The residue was purified by silica gel radial chromatography eluted with $CH_2Cl_2$. The fractions containing pure material were combined and concentrated in vacuo to afford 468 mg of the title compound as a white foam.

$^1$H-NMR (300 MHz, $CD_3OD$, ppm): δ1.20–1.40 (s, 9H), 1.45–1.65 (m, 4H), 2.20–2.60 (m, 2H), 3.45–3.70 (bs, 1H), 3.75–3.93 (dd, 2H), 4.25–4.45 (d, 1H), 4.50–4.4.65 (d, 1H), 7.10–7.43 (m, 5H), 7.45–7.70(m, 3H), 7.75–7.90 (dd, 2H). CI-MS m/e=431 (M+1).

Step E:

N'-benzyl-N'-phenylsulfonyl-3-amino-piperidine hydrochloride

A solution of the title compound in Step D (264 mg; 0.613 mmol) in cold saturated solution of HCl in THF (2 ml) was stirred at room temperarure for one hour. The solvent was removed in vacuo and the residue was triturated with EtOAc, filtered under $N_2$, washed with EtOAc, ether, and let dry under vacuo and $N_2$. The solid was dried in vacuo overnight to yield 206 mg of the title compound as a white solid.

$^1$H-NMR (300 MHz, $CD_3OD$, ppm): δ1.40–1.95 (m, 4H), 2.46–2.75 (t, 2H), 2.94–3.20 (m, 2H), 3.82–4.10 (m, 1H), 4.18–4.44 (d, 1H), 4.49–4.74 (d, 1H), 7.05–7.45 (m, 5H), 7.50–7.75 (m, 3H), 7.80–8.00 (dd, 2H). CI-MS m/e=331 (M+1).

EXAMPLE 2

N-Phenyl-N'-phenylsulfonyl-3-amino-piperidine hydrochloride

Step A:

N-(tert-Butoxycarbonyl)-N-phenyl-3-aminopiperidine

The titled compound was prepared from the product obtained in Step B of Example 1, using a procedure similar to that described in Step C of Example 1 replacing benzylamine with aniline as the amine source. Purification yields 522 mg (60%) of the title compound as a yellow solid, which was used as is in the next step.

Step B:

N-(tert-Butoxycarbonyl)-N-phenyl-N'-phenylsulfonyl-3-aminopiperidine

The titled product was prepared from the product obtained in Step A using the procedure in Step D of Example 1 to yield 530 mg (67%) of the titled compound as a white solid.

$^1$H-NMR (300 MHz, $CD_3OD$, ppm): δ1.03–1.32 (m, 1H), 1.35–1.55 (s, 9H), 1.55–1.70 (m, 2H), 2.15–2.60 (m, 2H), 3.70–3.94 (d, 1H), 3.97–4.16 (m, 1H), 4.17–4.30 (d, 1H), 6.85–7.03 (dd, 2H), 7.20–7.43 (m, 3H), 7.45–7.80 (m, 5H). CI-MS m/e=418 (M+1).

Step C:

N-phenyl-N'-phenylsulfonyl-3-aminopiperidine hydrochloride

The titled product was prepared from the product obtained in Step B using the procedure described in Step E of Example 1 to yield 403 mg of the titled compound as a white solid.

$^1$H-NMR (300 MHz, $CD_3OD$, ppm): δ1.15–1.40 (m, 1H), 1.70–2.05 (m, 3H), 2.55–2.65 (dd, 1H), 2.66–2.80 (t, 1H), 3.15–3.25 (dd, 1H), 3.45–3.60 (dd, 1H), 4.40–4.60 (m, 1H), 6.92–7.11 (dd, 2H), 7.18–7.45 (m, 3H), 7.47–7.80 (m, 5H). CI-MS m/e=318 (M+1).

EXAMPLE 3

The following general synthesis was applied for the preparation of all compounds listed in Table I below:

Step A:

A solution of the Intermediate 1 (or 3) (0.268 mmol) in $CH_2Cl_2$ (1 ml) was cooled to 0° C., to which was added the titled compound from Step E of Example 1 (or Step C of Example 2) (0.314 mmol). To the solution was then added HOBT (0.392 mmol), followed by NMM (0.527 mmol), and EDC (0.344 mmol). The reaction was stirred for one hour at room temperature, and then partitioned between $H_2O$ and EtOAc. The organic phase was washed with saturated aqueous $NaHCO_3$, $H_2O$, 10% aqueous citric acid, $H_2O$, saturated aqueous NaCl, dried ($MgSO_4$), filtered and evaporated. The residue was purified by silica gel radial chromatography eluted with 50% EtOAc-hexanes. The fractions containing pure compound were combined and concentrated in vacuo to afford the desired product as either a mixture of diastereoismers (1+2), or individual isomers (1 or 2).

Step B:

HCl(g) was bubbled into a solution of the product from Step A (0.108 mmol) in EtOAc (2 ml), and the reaction was stirrred at room temperature for one hour. The solvent was removed in vacuo, and the residue was triturated with ether, filtered under $N_2$, and dried in vacuo to yield the desired product as a white solid.

TABLE I

| Isomer | $R^a$ | $R^b$ | CI-MS (M + 1) | Log P (min) | Cpd # |
|---|---|---|---|---|---|
| Recemic | 3-Indolyl | —$CH_2Ph$ | 602 | 3.6 | 3a |
| Isomer 1 | 3-Indolyl | Ph | 588 | 3.2 | 3b |
| Isomer 2 | 3-Indolyl | Ph | 588 | 3.0 | 3c |
| Isomer 1 | $Ph(CH_2)_3$— | —$CH_2Ph$ | 591 | 4.4 | 3d |
| Isomer 2 | $Ph(CH_2)_3$— | —$CH_2Ph$ | 591 | 4.4 | 3e |
| Recemic | $Ph(CH_2)_3$— | Ph | 577 | 4.2 | 3f |
| Isomer 2 | $Ph(CH_2)_3$— | Ph | 577 | 4.0 | 3g |

TABLE II

| Cpd # | ¹H-NMR δ (400 MHz, CD₃OD, ppm) |
|---|---|
| 3a | −0.433−(−)0.151(m, 0.22H), 0.795−1.84(m, 11H), 1.89−2.08(m, 1.2H), 2.09−2.25(m, 0.37H), 2.35−2.57(m, 0.33H), 2.67−2.89(m, 0.26H), 2.94−3.26(m, 2.4H), 3.46−3.78(m, 1.45H), 3.79−3.95(m, 0.39H), 4.00−4.38(m, 2.57H), 4.44−4.62(m, 0.53H), 4.64−4.83(m, 0.41H), 4.94−5.17(m, 1.3H), 6.75−8.07(m, 15H). |
| 3b | 0.78−0.98(m, 0.4H), 1.02−1.26(m, 1.3H), 1.30−1.76(m, 8.8H), 1.77−2.01(m, 2.0H), 2.06−2.29(m, 0.45H), 2.76−2.99(m, 0.41H), 3.00−3.25(m, 1.9H), 3.34−3.81(m, 1.8H)3.97−4.15(m, 0.7H), 4.19−4.34(m, 0.5H), 4.37−4.51(m, 0.4H), 4.53−4.51(m, 0.6H), 4.98−5.29(m, 1.1H), 6.76−7.91(m, 15H). |
| 3c | −0.229−0.093(m, 0.11H), 0.854−1.13(m, 1.25H), 1.16−1.95 (m, 10.9H), 1.98−2.19(m, 0.25H), 2.34−2.52(m, 0.19H), 2.98−3.27(m, 2.7H), 3.49−3.69(m, 0.51H), 4.11−4.36(m, 1.47H), 4.53−4.70(m, 0.2H), 4.92−5.19(m, 1.24H), 6.24−6.49 (m, 1.3H), 6.77−6.98(m, 1.9H), 7.00−7.49(m, 6.49H), 7.51−7.98(m, 5.29H). |
| 3d | 0.736−1.06(m, 0.15H), 1.11−2.02(m, 16.3H), 2.09−2.41(m, 1.1H), 2.46−2.84(m, 3.62), 2.86−3.03(m, 2.1H), 3.05−3.27 (1.1H), 3.38−3.56(m, 0.49H), 3.60−3.80(m, 1.3H), 3.85−4.07 (m, 0.7H), 4.08−4.19(m, 0.3H), 4.22−4.49(m, 2.1H), 4.50−4.86(m, 1.6H), 6.98−7.50(m, 9.9H), 7.51−7.72(m, 2.9H), 7.74−8.03(m, 2.22H). |
| 3e | 0.864−1.07(m, 0.3H), 1.09−2.00(m, 16H), 2.13−2.38(m, 0.9H), 2.46−2.88(m, 3.6H), 3.04−3.26(m, 0.5H), 3.43−3.78 (m, 1.3H), 3.87−4.07(m, 0.8H), 4.09−4.19(m, 0.3H), 4.21−4.50(m, 2.2H), 4.52−4.78(m, 1.9H), 7.03−7.50(m, 9.9H), 7.51−7.56(m, 3.1H), 7.78−7.93(m, 1.1H), 7.95−8.12(m, 0.9H). |
| 3f | 1.02−1.49(m, 2H), 1.52−2.13(m, 14H), 2.16−2.43(m, 1H), 2.48−2.93(m, 3.3H), 2.96−3.13(m, 0.3H), 3.15−3.25(m, 0.2H), 3.43−3.83(m, 0.8H), 3.90−4.74(m, 3H), 4.74−4.84(m, 0.5H), 4.92−5.01(m, 0.4H), 6.87−8.04(m, 15H). |
| 3g | 0.991−2.06(m, 16.7H), 2.14−2.38(m, 0.8H), 2.49−2.95(m, 2.5H), 3.47−3.72(m, 0.55H), 3.89−4.21(m, 1H), 4.23−4.46(m, 1.2H), 4.48−4.58(m, 0.2H), 4.59−4.70(0.37H), 4.72−4.82(m, 0.5H), 6.86−8.04(15H). |

EXAMPLE 4

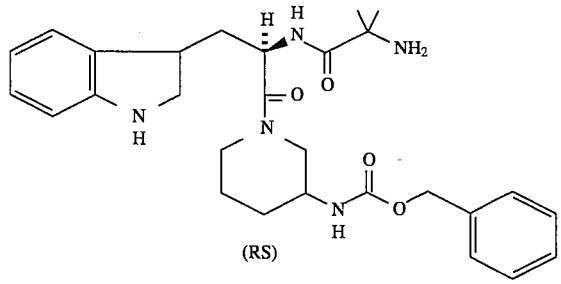

(RS)

Step A:

Racemic N-(tert-Butoxycarbonyl)-3-(N'-[carbobenzoxy])-piperidine

To a solution of racemic N-Boc nipecotic acid (230 mg; 1 mmol) in toluene (12 ml) under nitrogen was added diphenylphosphoryl azide (DPPA) (259 μl; 1.2 mmol) and triethylamine (TEA) (170 μl; 1.22 mmol). The reaction was refluxed under nitrogen for one hour. The solvent was removed in vacuo, CH₂Cl₂ (20 ml) and THF (20 ml) were added to the residue, followed by benzyl alcohol (115 μl; 1.5 mmol) and DMAP (122 mg; 1 mmol). The solution was refluxed overnight, and then concentrated in vacuo to yield a residue which was partitioned between H₂O and EtOAc. The aqueous phase was extracted once more EtOAc, and the combined organic extracts was washed with 10% aqueous NaHCO₃, H₂O, 10% aqueous citric acid, H₂O, saturated aqueous NaCl, dried (MgSO₄), filtered and evaporated. The crude oil was purified by silica gel radial chromatography eluted with EtOAc-hexanes (25:75) to yield 150 mg of the titled compound.

¹H-NMR (300 MHz, CD₃OD, ppm): δ1.3−1.5 (s, 11H), 1.61−2.15 (m, 3H), 2.19−2.58 (m, 2H), 2.67−2.87 (m, 1H), 2.91−3.11 (m, 1H), 3.31−3.60 (m, 1H), 5.17 (s, 2H), 7.00−7.60 (m, 5H).

Step B:

Racemic 3-(N-Carbobenzoxy)piperidine hydrochloride

The titled compound was prepared from the product obtained in Step A using a procedure similar to that of Step E in Example 1. Purification yields 115 mg of the titled compound as a white solid.

¹H-NMR (300 MHz, CD₃OD, ppm): δ1.09−2.72 (m, 3H), 1.76−1.99 (m, 1H), 2.18−2.59 (m, 2H), 2.67−2.87 (m, 1H), 2.91−3.11 (m, 1H), 3.31−3.60 (m, 1H), 4.89−5.17 (s, 2H), 7.00−7.60 (m, 5H). CI-MS m/e: 235 (M+1).

Step C:

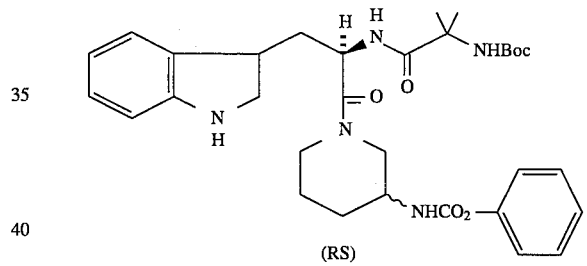

(RS)

The product of Step B was coupled with Intermediate 1 as decribed in Step A of Example 3 to provide the desired compound (a mixture of diastereoisomer) as a white solid.

¹H-NMR (400 MHz, CD₃OD, ppm): δ0.736−0.991 (m, 4H), 1.04−1.89 (m, 24H), 2.21−2.42 (m, 0.7H), 2.50−2.80 (m, 1.4H), 2.84−3.25 (m, 3.7H), 3.30−3.78 (m, 3H), 3.96−4.22 (m, 0.7H), 4.95−5.33 (m, 3.7H), 6.84−7.73 (m, 10H). ESI-MS m/e: 606 (M+1).

Step D:

The compound (50 mg) obtained in Step C was dissolved in dry ethylacetate (1ml) saturated with HCl(g) at room temperature. The mixture was stirred at that temperature for 1 h. The product was precipitated from the reaction with dry ether and filtered. The title compound was obtained as a hydrochloride salt (white solid). Yield 35 mg. ¹H-NMR (400 MHz, CD₃OD, ppm): δ0.74−0.96 (m, 4H), 1.0−1.89 (m, 15H), 2.21−2.42 (m, 0.7H), 2.50−2.80 (m, 1.4H), 2.84−3.25 (m, 3.7H), 3.30−3.78 (m, 3H), 3.96−4.22 (m, 0.7H), 4.95−5.33 (m, 3.7H), 6.84−7.73 (m, 10H). ESI-MS m/e: 506 (M+1).

EXAMPLE 5

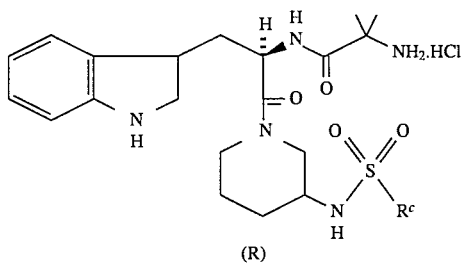
(R)

Step A:

N-(tert-Butoxycarbonyl)-(R)-nipecotic acid.

To solution of racemic N-Boc-nipecotic acid (15 g) in ethylacetate (500 ml) was slowly added (S)-α-methyl benzylamine (12. 25 ml) at room temperature, and stirring continued at that temperature for 1 h. The precepitate formed was filtered, washed with ethylacetate (30 ml) and dried (10 g), and then crystallized from ethylacetate containing 10% methanol. The crystallized material was filtered, washed with ethyl acetate and dried. Yield: 7.6 g; mp: 176°–178° C. The ethyl acetate suspension of the salt was treated with aqueous 10% citric acid. The organic phase was then washed with water, dried (MgSO$_4$) and concentrated in vacuo to provide the pure R-acid as a white solid (5.1 mg). mp: 168°–169° C.; $[\alpha]_D$=+48.3° (c=1, MeOH).

Step B:

3-(R)-(N-Carbobenzoxyl)piperidine hydrochloride

The titled compound was prepared from the product (230 mg) obtained in Step A using a procedure similar to that described in Steps A and B of Example 4. Purification yields 115 mg of the titled compound as a white solid.

$^1$H-NMR (300 MHz, CD$_3$OD, ppm): δ1.09–2.72 (m, 3H), 1.76–1.99 (m, 1H), 2.18–2.59 (m, 2H), 2.67–2.87 (m, 1H), 2.91–3.11 (m, 1H), 3.31–3.60 (m, 1H), 4.89–5.17 (s, 2H), 7.00–7.60 (m, 5H). CI-MS m/e:235 (M+1).

Step C:

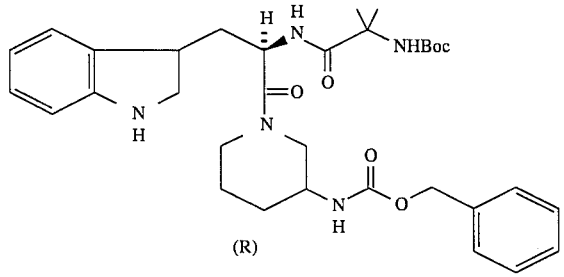
(R)

The above compound was prepared from the product of Step B using the procedure described in Step C of Example 4.

$^1$H-NMR (400 MHz, CD$_3$OD, ppm): δ0.736–0.991 (m, 0.4H), 1.04–1.89 (m, 24H), 2.21–2.42 (m, 0.7H), 2.50–2.80 (m, 1.4H), 2.84–3.25 (m, 3.7H), 3.30–3.78 (m, 3H), 3.96–4.22 (m, 0.7H), 4.95–5.33 (m, 3.7H), 6.84–7.73 (m, 10H). ESI-MS m/e: 606 (M+1).

Step D:

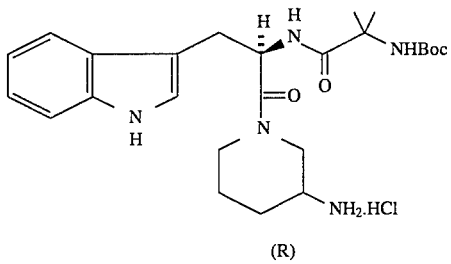
(R)

To a solution of the titled compounds in Step C (320 mg; 0.531 mmol) in MeOH (10 ml) and CHCl$_3$ (200 μl), was added Pd/C (46 mg), and the mixture was stirred in an atmosphere of H$_2$ for two days. The mixture was then filtered through a pad of celite, and the filtrate was concentrated in vacuo to yield 260 mg of the titled compound.

$^1$H-NMR (300 MHz, CD$_3$OD, ppm): δ0.053–0.404 (m, 0.15H), 1.02–1.81 (m, 20H), 1.85–2.07 (m, 0.4H), 2.11–2.46 (m, 1H), 2.74–3.21 (m, 4H), 3.78–4.11 (m, 0.7H), 4.21–4.43 (m, 0.2H), 4.92–5.20 (m, 1H), 6.81–7.96 (m, 5H).

Step E:

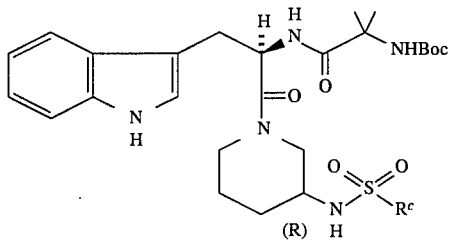

The product from Step D was reacted with appropriate sulfonyl chlorides, using the conditions described in Step D of Example 1, to provide the desired protected sulfonamides. The compounds were purified by silica-gel radial chromatography using EtOAc-hexanes (66:33) to yield the title compounds as a white solid.

Step F:.

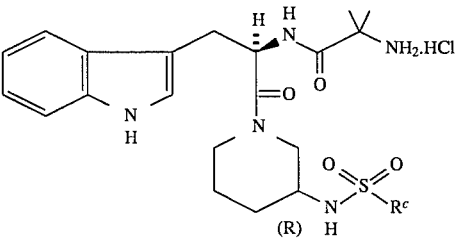

The compounds prepared in Step E were deprotected with HCl/EtOAc, as described in Step B of Example 2, to provide titled compounds (Tables III and IV).

The corresponding S-isomers (described in Tables III & IV) were made similarly starting with N-(tert-butoxycarbonyl)-(S)-nipecotic acid.

N-(tert-butoxycarbonyl)-(S)-nipecotic acid was prepared from racemic N-BOC-neipecotic acid using (R)-α-methylbenzyl amine as the resolving agent as described in Step A.

mp. 170°–171° C.; [α]$_D$=–48.6° (c=1, MeOH).

TABLE III

| Isomer | Cpd # | R$^c$ | CI-MS (M$^+$) | Mol. formula |
|---|---|---|---|---|
| R | 5a | Ph | 512 | C$_{26}$H$_{33}$N$_5$SO$_4$ |
| S | 5b | Ph | 512 | C$_{26}$H$_{33}$N$_5$SO$_4$ |
| R | 5c | quinol-8-yl | 563 | C$_{29}$H$_{34}$N$_6$SO$_4$ |
| S | 5d | quinol-8-yl | 563 | C$_{29}$H$_{34}$N$_6$SO$_4$ |

TABLE IV

| Cpd # | $^1$H-NMRδ (400 MHz, CD$_3$OD, ppm) |
|---|---|
| 5a | 0.834–1.92(m, 11H), 2.14–2.51(m, 1H), 2.69–3.25(m, 5H), 3.46–3.70(m, 0.7H), 4.00–4.44(m, 0.7H), 4.69–4.84(m, 0.7H), 4.99–5.25(m, 0.6H), 6.82–8.03(m, 10H), 8.09–8.47(0.3H). |
| 5b | –0.102–0.147(m, 0.12H), 0.806–1.90(m, 10H), 2.07–2.35(m, 0.9H), 2.38–2.64(m, 0.8H), 2.67–2.91(m, 0.5H), 2.98–3.25 (m, 2.5H), 3.58–3.84(m, 0.46H), 4.01–4.32(m, 0.85H), 4.99–5.26(m, 0.77H), 6.85–8.03(m, 10H), 8.08–8.37(m, 0.3H). |
| 5c | 0.785–1.83(m, 13H), 2.39–2.68(m, 0.9H), 2.78–3.27(m, 4.5H), 3.88–4.12(m, 0.6H), 4.99–5.22(m, 0.5H), 6.69–7.56(m, 5H), 7.66–8.11(m, 2H), 8.18–8.67(m, 2H), 8.70–8.87(m, 0.5H), 8.89–9.12(m, 0.9H), 9.16–9.39(m, 0.4H). |
| 5d | –0.10–0.305(m, 0.1H), 0.803–1.798(m, 11H), 2.37–3.25(m, 4.2H), 3.37–4.00(m, 1.3H), 4.97–5.19(m, 0.6H), 6.69–7.61(m, 5H), 7.68–8.11(m, 2H), 8.16–8.77(m, 2.3H), 8.79–9.05(0.9H), 9.07–9.36(m, 0.9H). |

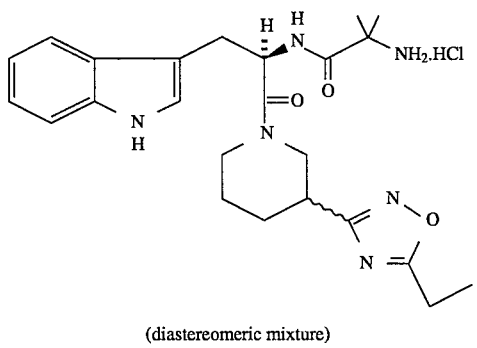

(diastereomeric mixture)

To a solution of 20 mg of Intermediate 1, 0.020 mL of N-methylmorpholine, 20 mg of EDC and 20 mg of HOBT in 2 mL of CH$_2$Cl$_2$ was added 11 mg of 3-(5-ethyl-1,2,4-oxadiazolyl)piperidine hydrochloride and stirred for a day at room temperature (the piperidine hydrochloride was prepared in 3 steps from N-t-BOC protected 3-cyanopiperidine by a) addition of hydroxylamine to the nitrile in refluxing methanol, b) acylation of the amino-oxime with propionyl-chloride in pyridine, and c) deprotection of the N-t-BOC protecting group with HCl (gas) in ethyl acetate). The reaction mixture was poured into 5 mL of CH$_2$Cl$_2$ and washed with (2×3 mL) of 0.50N HCl solution, 3 mL of 1N aqueous sodium hydroxide solution, dried over anhydrous magnesium sulfate, filtered and concentrated to give a thick oil. Flash chromatography of this material (10 g silica gel; hexane:acetone (5:1) as the eluent) gave 13.6 mg of the coupled product as a diastereomeric mixture. This material was deprotected by treating an EtOAc solution with dry HCl (gas) for 5 min. Ether was added and the precipitate was collected under nitrogen and dried. The title compound was a white to off-white solid. FAB-MS m/e: 453.59 (M+1).

EXAMPLE 7

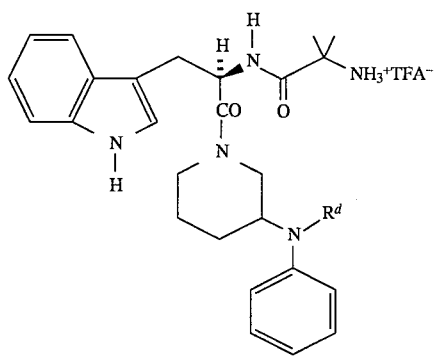

Step A:

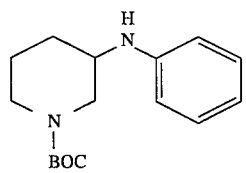

The title compound was prepared by the methodology of Example 2, Step A.

Step B:

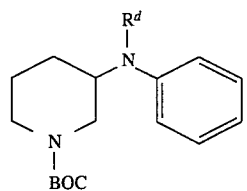

To a solution of the amine from Step A (300 mg; 1.1 mmol) in CH$_2$Cl$_2$ (5.0 mL) was added triethylamine (1.5 mL; 10.8 mmol), DMAP (catalytic) and acetic anhydride (0.5 mL; 5.4 mmol). The mixture was refluxed until complete by TLC analysis whereupon the reaction was diluted with ethyl acetate, washed with 2N HCl, saturated potassium carbonate, water, brine, dried (K$_2$CO$_3$) and concentrated. Radial chromatography (2 mm plate; 4:1 hexanes:ethyl acetate) of the residue gave the compounds of Table V.

The sulfonamides of Table V (7B-6 to 9) were prepared essentially in the manner described in Example 1, Step D using known sulfonyl chlorides.

TABLE V

| Example # | R$^d$ | Mass Spectral Data |
|---|---|---|
| 7B-1 | hydrogen | — |
| 7B-2 | (C(=O)CH$_3$) | 218.2 (MH$^+$ – CO$_2$-t-Bu) |
| 7B-3 | (C(=O)CH(CH$_3$)$_2$) | 247.2 (MH$^+$ – CO$_2$-t-Bu) |

TABLE V-continued

| Example # | R$^d$ | Mass Spectral Data |
|---|---|---|
| 7B-4 | (cyclohexyl methyl ketone) | 287.3 (MH$^+$—CO$_2$-t-Bu) |
| 7B-5 | (phenyl methyl ketone) | 281.2 (MH$^+$—CO$_2$-t-Bu) |
| 7B-6 | —SO$_2$CH$_3$ | 255 (MH$^+$—CO$_2$-t-Bu) |
| 7B-7 | —SO$_2$Ph | — |
| 7B-8 | —SO$_2$CH(CH$_3$)$_2$ | 283 (MH$^+$—CO$_2$-t-Bu) |
| 7B-9 | —SO$_2$-t-Bu | 297 (MH$^+$—CO$_2$-t-Bu) |
| 7B-10 | —C(O)NH$_2$ | (ND) |
| 7B-11 | —C(O)NHCH$_3$ | (ND) |
| 7B-12 | —C(O)NHCH(CH$_3$)$_2$ | (ND) |
| 7B-13 | —C(O)NHPh | (ND) |

Step C:

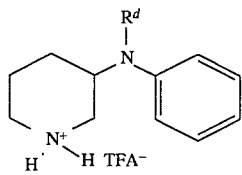

The appropriate N-BOC derivatives were deprotected in the general manner described herein with trifluoroacetic acid in dichloromethane at 0° C. to give the amine salts of Table VI.

TABLE VI

| Example # | R$^d$ | Mass Spectral Data |
|---|---|---|
| 7C-1 | hydrogen | — |
| 7C-2 | (methyl ketone) | 219.2 (MH$^+$) |
| 7C-3 | (isopropyl ketone) | 246.33 (MH$^+$) |
| 7C-4 | (cyclohexyl methyl ketone) | 287.3 (MH$^+$) |
| 7C-5 | (phenyl methyl ketone) | 281.2 (MH$^+$) |
| 7C-6 | —SO$_2$CH$_3$ | 255 (MH$^+$) |
| 7C-7 | —SO$_2$Ph | — |
| 7C-8 | —SO$_2$CH(CH$_3$)$_2$ | 283 (MH$^+$) |
| 7C-9 | —SO$_2$-t-Bu | 297 (MH$^+$) |
| 7C-10 | —C(O)NH$_2$ | (ND) |

TABLE VI-continued

| Example # | R$^d$ | Mass Spectral Data |
|---|---|---|
| 7C-11 | —C(O)NHCH$_3$ | (ND) |
| 7C-12 | —C(O)NHCH(CH$_3$)$_2$ | (ND) |
| 7C-13 | —C(O)NHPh | (ND) |

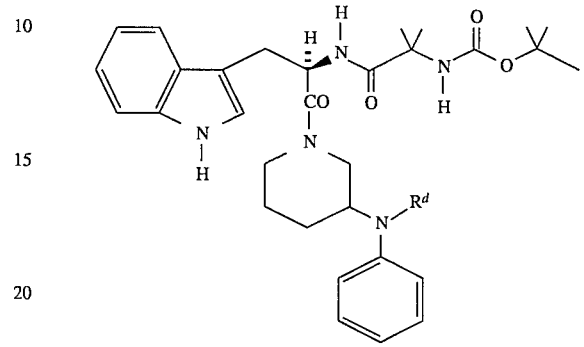

To a solution of the appropriate amine salt (1 equivalent) from Step C in dichloromethane was added N-methyl morpholine (1 equivalent) and the mixture was stirred 10 minutes. To this mixture was added d-TRP-BocAIB (1 equivalent), HOBT (1 equivalent) and EDCI (2 equivalents). The reaction was stirred until complete by TLC analysis whereupon the reaction was worked up in the general manner described herein and the chromatographed in the general manner described herein to give the compounds of Table VII.

TABLE VII

| Example # | R$^d$ | Mass Spectral Data |
|---|---|---|
| 7D-1 | hydrogen | 548.3 (MH$^+$) |
| 7D-2 | (methyl ketone) | 514.7 (MH$^+$—O-t-Bu) |
| 7D-3 | (isopropyl ketone) | 544.3 (MH$^+$—O-t-Bu) |
| 7D-4 | (cyclohexyl methyl ketone) | 584.4 (MH$^+$—O-t-Bu) |
| 7D-5 | (phenyl methyl ketone) | 578.3 (MH$^+$—O-t-Bu) |
| 7D-6 | —SO$_2$CH$_3$ | 526 (MH$^+$—CO$_2$-t-Bu) |
| 7D-7 | —SO$_2$Ph | — |
| 7D-8 | —SO$_2$CH(CH$_3$)$_2$ | 554 (MH$^+$—CO$_2$-t-Bu) |
| 7D-9 | —SO$_2$-t-Bu | 568 (MH$^+$—CO$_2$-t-Bu) |
| 7D-10 | —C(O)NH$_2$ | (ND) |
| 7D-11 | —C(O)NHCH$_3$ | (ND) |
| 7D-12 | —C(O)NHCH(CH$_3$)$_2$ | (ND) |
| 7D-13 | —C(O)NHPh | (ND) |

Step E:

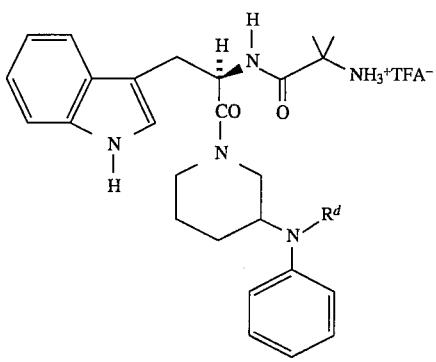

The appropriate N-BOC derivatives from Step D were deprotected in the general manner described herein with trifluoroacetic acid in dichloromethane at 0° C. to give the amine salts of Table VIII.

TABLE VIII

| Example # | $R^d$ | Mass Spectral Data |
|---|---|---|
| 7E-1 | hydrogen | 448.3 (MH+) |
| 7E-2 | —C(O)CH$_3$ | — |
| 7E-3 | —C(O)CH(CH$_3$)$_2$ | 518.2 (MH+) |
| 7E-4 | —C(O)-cyclohexyl | 558.3 (MH+) |
| 7E-5 | —C(O)Ph | 552.3 (MH+) |
| 7E-6 | —SO$_2$CH$_3$ | 526 (MH+) |
| 7E-7 | —SO$_2$Ph | — |
| 7E-8 | —SO$_2$CH(CH$_3$)$_2$ | 554 (MH+) |
| 7E-9 | —SO$_2$-t-Bu | 568 (MH+) |
| 7E-10 | —C(O)NH$_2$ | (ND) |
| 7E-11 | —C(O)NHCH$_3$ | (ND) |
| 7E-12 | —C(O)NHCH(CH$_3$)$_2$ | (ND) |
| 7E-13 | —C(O)NHPh | (ND) |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula:

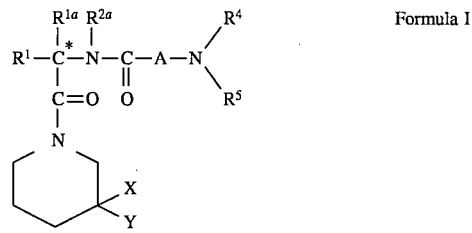

Formula I wherein:

$R^1$ is selected from the group consisting of: $C_1$–$C_{10}$ alkyl, aryl, aryl($C_1$–$C_6$ alkyl), ($C_3$–$C_7$ cycloalkyl)($C_1$–$C_6$ alkyl)-, ($C_1$–$C_5$ alkyl)-K-($C_1$–$C_5$ alkyl)-, aryl($C_0$–$C_5$ alkyl)-K-($C_1$–$C_5$ alkyl)-, and ($C_3$–$C_7$ cycloalkyl)($C_0$–$C_5$ alkyl)-K-($C_1$–$C_5$ alkyl)-, where K is —O—, —S(O)$_m$—, —N($R^2$)C(O)—, —C(O)N($R^2$)—, —OC(O)—, —C(O)O—, —$CR^2$=$CR^2$—, or —C≡C—, where aryl is selected from: phenyl, naphthyl, indolyl, azaindole, pyridyl, benzothienyl, benzofuranyl, thiazolyl, and benzimidazolyl, and $R^2$ and alkyl may be further substituted by 1 to 9 halogen, $S(O)_m R^{2a}$, 1 to 3 of $OR^{2a}$ or $C(O)OR^{2a}$, and aryl may be further substituted by 1 to 3 of $C_1$–$C_6$ alkyl, 1 to 3 of halogen, 1 to 2 of —$OR^2$, methylenedioxy, —$S(O)_m R^2$, 1 to 2 of —$CF_3$, —$OCF_3$, nitro, —N($R^2$)C(O)($R^2$), —C(O)$OR^2$, —C(O)N($R^2$)($R^2$), —1H-tetrazol-5-yl, —SO$_2$N($R^2$)($R^2$), —N($R^2$)SO$_2$ phenyl, or —N($R^2$)SO$_2$$R^2$;

$R^{1a}$ is selected from hydrogen and $C_1$–$C_6$ alkyl;

$R^2$ is selected from: hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl;

$R^{2a}$ is selected from hydrogen and $C_1$–$C_6$ alkyl;

$R^4$ and $R^5$ are independently hydrogen, $C_1$–$C_6$ alkyl, or substituted $C_1$–$C_6$ alkyl where the substituents are selected from: 1 to 5 halo, 1 to 3 hydroxy, 1 to 3 $C_1$–$C_{10}$ alkanoyloxy, 1 to 3 $C_1$–$C_6$ alkoxy, phenyl, phenyloxy, 2-furyl, $C_1$–$C_6$ alkoxycarbonyl, $S(O)_m (C_1$–$C_6$ alkyl), or $R^4$ and $R^5$ may be taken together to form —(CH$_2$)$_d$-$L_a$(CH$_2$)$_e$— where $L_a$ is —C($R^2$)$_2$—, —O—, —S(O)$_m$— or —N($R^2$)—, d and e are independently 1 to 3 and $R^2$ is as defined above;

X is selected from the group consisting of: —(CH$_2$)$_q$N($R^8$)C(O)$R^2$, —(CH$_2$)$_q$N($R^8$)C(O)$R^8$, —(CH$_2$)$_q$N($R^8$)C(O)$OR^2$, —(CH$_2$)$_q$N($R^8$)C(O)$OR^8$, —(CH$_2$)$_q$N($R^8$)C(O)$OR^2$, —(CH$_2$)$_q$N($R^2$)C(O)$OR^8$, —(CH$_2$)$_q$N($R^8$)C(O)$OR^8$, —(CH$_2$)$_q$N($R^2$)SO$_2$$R^9$, —(CH$_2$)$_q$N($R^8$)SO$_2$$R^8$, —(CH$_2$)$_q$N($R^8$)SO$_2$$R^2$, —(CH$_2$)$_q$N($R^2$)SO$_2$N($R^2$)($R^8$), —(CH$_2$)$_q$N($R^8$)C(O)N($R^2$)($R^2$), —(CH$_2$)$_q$N($R^8$)C(O)N($R^2$)($R^8$), —(CH$_2$)$_q$SO$_2$N($R^2$)($R^2$), —(CH$_2$)$_q$SO$_2$N($R^2$)($R^8$), —(CH$_2$)$_q$N($R^2$)($R^8$), and —(CH$_2$)$_q$$R^{10}$, where the $R^2$ and (CH$_2$)$_q$ groups may be optionally substituted by 1 to 2 $C_1$–$C_4$ alkyl, hydroxyl, $C_1$–$C_4$ lower alkoxy, carboxyl, $CONH_2$, $S(O)_mCH_3$, carboxylate $C_1$–$C_4$ alkyl esters, or 1H-tetrazol-5-yl;

Y is selected from the group consisting of: hydrogen, $C_1$–$C_{10}$ alkyl, —$(CH_2)_t$aryl, —$(CH_2)_q(C_3$–$C_7$ cycloalkyl), —$(CH_2)_q$—K—$(C_1$–$C_6$ alkyl), —$(CH_2)_q$—K—$(CH_2)_t$aryl, —$(CH_2)_q$—K—$(CH_2)_t(C_3$–$C_7$ cycloalkyl containing —O—, —$NR^2$—, or —S—), and —$(CH_2)_q$—K—$(CH_2)_t(C_3$–$C_7$ cycloalkyl), where K is as defined above, and where the alkyl, $R^2$, $(CH_2)_q$ and $(CH_2)_t$ groups may be optionally substituted by $C_1$–$C_4$ alkyl, hydroxyl, $C_1$–$C_4$ lower alkoxy, carboxyl, —$CONH_2$ or carboxylate $C_1$–$C_4$ alkyl esters, and where aryl is phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrazinyl, or isothiazolyl which is optionally substituted by 1 to 3 halogen, 1 to 3 —$OR^2$, —$C(O)OR^2$, —$C(O)N(R^2)(R^2)$, nitro, cyano, benzyl, 1 to 3 $C_1$–$C_4$ alkyl, —$S(O)_mR^2$, or 1H-tetrazol-5-yl;

A is:

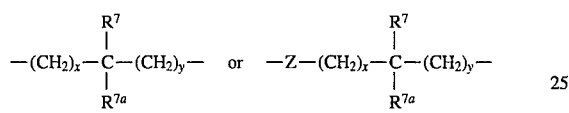

where x and y are independently 0, 1, 2 or 3;

Z is —$N(R^{6a})$— or —O—, where $R^{6a}$ is hydrogen or $C_1$–$C_6$ alkyl;

$R^7$ and $R^{7a}$ are independently hydrogen, $C_1$–$C_6$ alkyl, trifluoromethyl, phenyl, or substituted $C_1$–$C_6$ alkyl where the substituents are imidazolyl, naphthyl, phenyl, indolyl, p-hydroxyphenyl, —$OR^2$, —$S(O)_mR^2$, —$C(O)OR^2$, $C_3$–$C_7$ cycloalkyl, —$N(R^2)(R^2)$, —$C(O)N(R^2)(R^2)$, or $R^7$ and $R^{7a}$ may independently be joined to one or both of $R^4$ and $R^5$ groups to form an alkylene bridge between the terminal nitrogen and the alkyl portion of the $R^7$ or $R^{7a}$ groups, wherein the bridge contains 1 to 5 carbons atoms, or $R^7$ and $R^{7a}$ can be joined to one another to form $C_3$–$C_7$ cycloalkyl;

$R^8$ is —$(CH_2)_p$aryl, where aryl is selected from: phenyl, naphthyl, pyridyl, thiazolyl, isothiazolyl, oxazolyl, isoxazolyl, thienyl, pyrazinyl, pyrimidinyl, benzothienyl, benzofuranyl, benzimidazolyl, imidazolyl, indolyl, quinolinyl, and isoquinolinyl, and where the aryl is optionally substituted with 1 to 2 of halogen, —$R^2$, —$OR^2$, —$N(R^2)(R^2)$, —$C(O)OR^2$, or —$C(O)N(R^2)(R^2)$;

$R^9$ is selected from the group consisting of: isoxazolyl, thiazolyl, isothiazolyl, thienyl, benzothienyl, benzofuranyl, benzimidazolyl, imidazolyl, indolyl, quinolinyl, and isoquinolinyl, which are optionally substituted by 1 to 2 of halogen, —$R^2$, —$OR^2$, —$N(R^2)(R^2)$, —$C(O)OR^2$, or —$C(O)N(R^2)(R^2)$;

$R^{10}$ is selected from the group consisting of: 1,2,4-oxadiazolyl, pyrazinyl, triazolyl, and phthalimidoyl, which are optionally substituted with —$R^2$, —$OR^2$ or —$N(R^2)(R^2)$;

m is 0, 1, or 2;

p is 0, 1, 2, or 3;

q is 0, 1, 2, 3, or 4;

t is 0, 1, 2, or 3;

and pharmaceutically acceptable salts and individual diastereomers thereof.

2. The compound of claim 1 of the formula:

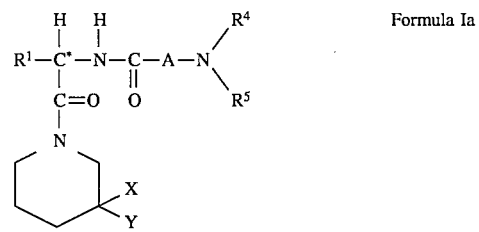

Formula Ia wherein:

$R^1$ is selected from the group consisting of: $C_1$–$C_{10}$ alkyl, aryl ($C_1$–$C_4$ alkyl)-, $C_3$–$C_6$ cycloalkyl ($C_1$–$C_4$ alkyl)-, ($C_1$–$C_4$ alkyl)-K-($C_1$–$C_2$ alkyl)-, aryl ($C_0$–$C_2$ alkyl)-K-($C_1$–$C_2$ alkyl)-, and ($C_3$–$C_7$ cycloalkyl)($C_0$–$C_2$ alkyl)-K-($C_1$–$C_2$ alkyl)-, where K is —O—, —$S(O)_m$—, —$OC(O)$—, or —$C(O)O$—, and the alkyl groups may be further substituted by 1 to 7 halogen, —$S(O)_mR^2$, 1 to 3 —$OR^2$ or —$C(O)OR^2$, and aryl is phenyl, naphthyl, indolyl, pyridyl, benzimidazolyl, azaindolyl, benzothienyl or benzofuranyl which may be further substituted by 1–2 $C_1$–$C_4$ alkyl, 1 to 2 halogen, 1 to 2 —$OR^2$, —$S(O)_mR^2$, or —$C(O)OR^2$;

$R^2$ is hydrogen, $C_1$–$C_6$ alkyl, or $C_3$–$C_7$ cycloalkyl, and where two $C_1$–$C_6$ alkyl groups are present on one atom they may be optionally joined to form a $C_4$–$C_7$ cyclic ring optionally including oxygen, sulfur or $NR^{3a}$;

$R^4$ and $R^5$ are independently hydrogen, $C_1$–$C_6$ alkyl, or substituted $C_1$–$C_6$ alkyl where the substituents are 1 to 5 halo, 1 to 3 hydroxyl, —$S(O)_m$ ($C_1$–$C_6$ alkyl) or phenyl;

X is selected from the group consisting of: —$(CH_2)_qN(R^8)C(O)R^2$, —$(CH_2)_qN(R^8)C(O)R^8$, —$(CH_2)_qN(R^8)C(O)OR^2$, —$(CH_2)_qN(R^8)C(O)OR^8$, —$(CH_2)_qN(R^8)C(O)OR^2$, —$(CH_2)_qN(R^2)C(O)OR^8$, —$(CH_2)_qN(R^8)C(O)OR^8$, —$(CH_2)_qN(R^2)SO_2R^9$, —$(CH_2)_q$ $N(R^8)SO_2R^8$, —$(CH_2)_qN(R^8)SO_2R^2$, —$(CH_2)_qN(R^2)SO_2N(R^2)(R^8)$, —$(CH_2)_qN(R^8)C(O)N(R^2)(R^2)$, —$(CH_2)_qN(R^8)C(O)N(R^2)(R^8)$, —$(CH_2)_qSO_2N(R^2)(R^2)$, —$(CH_2)_qSO_2N(R^2)(R^8)$, —$(CH_2)_qN(R^2)(R^8)$, and —$(CH_2)_q R^{10}$, where the $R^2$, and $(CH_2)_q$ groups are optionally substituted by 1 to 2 $C_1$–$C_4$ alkyl, hydroxyl, $C_1$–$C_4$ lower alkoxy, carboxyl, $CONH_2$, $S(O)_mCH_3$, carboxylate $C_1$–$C_4$ alkyl esters, or 1H-tetrazol-5-yl;

Y is selected from the group consisting of: hydrogen, $C_1$–$C_8$ alkyl, $(CH_2)_t$aryl, —$(CH_2)_q(C_5$–$C_6$ cycloalkyl), —$(CH_2)_q$—K—$(C_1$–$C_6$ alkyl), —$(CH_2)_q$-K-$(CH_2)_t$aryl, —$(CH_2)_q$—K—$(CH_2)_t(C_3$–$C_7$ cycloalkyl containing —O—, —$NR^2$—, or —S—), and —$(CH_2)_q$—K—$(CH_2)_t$ $(C_5$–$C_6$ cycloalkyl), where K is —O— or —$S(O)_m$— and where the alkyl groups are optionally substituted by hydroxyl, carboxyl, $CONH_2$, carboxylate $C_1$–$C_4$ alkyl esters or 1H-tetrazole-5-yl and aryl is phenyl, naphthyl, pyridyl, 1-H-tetrazolyl, thiazolyl, imidazolyl, indolyl, pyrimidinyl, thiadiazolyl, pyrazolyl, oxazolyl, isoxazolyl, or thiopheneyl which is optionally substituted by 1 to 3 halogen, 1 to 3 —$OR^2$, —$C(O)OR^2$, —$C(O)N(R^2)(R^2)$, cyano, 1 to 2 $C_1$–$C_4$ alkyl, benzyl, —$S(O)_mR^2$, or 1H-tetrazol-5-yl-;

A is:

$$-(CH_2)_x-\underset{R^{7a}}{\overset{R^7}{\underset{|}{\overset{|}{C}}}}-(CH_2)_y- \text{ or } -Z-(CH_2)_x-\underset{R^{7a}}{\overset{R^7}{\underset{|}{\overset{|}{C}}}}-(CH_2)_y-$$

where x and y are independently 0, 1 or 2;

Z is $-NR^{6a}-$ or $-O-$, where $R^{6a}$ is hydrogen or $C_1$–$C_3$ alkyl;

$R^7$ and $R^{7a}$ are independently hydrogen $C_1$–$C_6$ alkyl, trifluoromethyl, phenyl, substituted $C_1$–$C_6$ alkyl where the substituents are imidazolyl, naphthyl, phenyl, indolyl, p-hydroxyphenyl, $OR^2$, $S(O)_mR^2$, $C(O)OR^2$, $C_5$–$C_7$ cycloalkyl, $-N(R^2)(R^2)$, $-C(O)N(R^2)(R^2)$; or $R^7$ and $R^{7a}$ can independently be joined to one of $R^4$ or $R^5$ to form alkylene bridges between the terminal nitrogen and the alkyl portion of $R^7$ or $R^{7a}$ groups to form 5 or 6 membered rings; or $R^7$ and $R^{7a}$ can be joined to one another to form a $C_3$ cycloalkyl;

$R^8$ is $-(CH_2)_p$aryl, where aryl is selected from: phenyl, naphthyl, pyridyl, thiazolyl, isothiazolyl, oxaxolyl, isoxazolyl, thienyl, pyrazinyl, pyrimidinyl, benzothienyl, benzofuranyl, benzimidazolyl, imidazolyl, indolyl, quinolinyl, and isoquinolinyl, and where aryl may be substituted by 1 to 2 of halogen, $-R^2$, $-OR^2$, $-N(R^2)(R^2)$, $-C(O)OR^2$, or $-C(O)N(R^2)(R^2)$;

$R^9$ is selected from the group consisting of: isoxazolyl, thiazolyl, isothiazolyl, thienyl, benzothienyl, benzofuranyl, benzimidazolyl, imidazolyl, indolyl, quinolinyl, and isoquinolinyl, which may be substituted by 1 to 2 of halogen, $-R^2$, $-OR^2$, $-N(R^2)(R^2)$, $-C(O)OR^2$, or $-C(O)N(R^2)(R^2)$;

$R^{10}$ is selected from the group consisting of: 1,2,4-oxadiazolyl, pyrazinyl, triazolyl, and phthalimidoyl, which are optionally substituted with $-R^2$, $-OR^2$ or $-N(R^2)(R^2)$;

m is 0, 1 or 2;

p is 0, 1 or 2;

q is 0, 1 or 2;

t is 0, 1 or 2;

and pharmaceutically acceptable salts and individual diastereomers thereof.

3. The compound of claim 1 of the formula:

$$\underset{\underset{N}{\underset{|}{\overset{|}{\text{C}=O}}}}{\overset{H}{\underset{|}{R^1-\overset{*}{C}}}}-\overset{H}{\underset{|}{N}}-\overset{O}{\underset{||}{C}}-A-N\diagdown_{R^5}^{R^4} \quad \text{Formula 1b}$$

(ring with X, Y)

wherein:

$R^1$ is selected from the group consisting of: $C_1$–$C_{10}$ alkyl, aryl ($C_1$–$C_3$ alkyl)-, ($C_3$–$C_7$ cycloalkyl)($C_1$–$C_3$ alkyl)-, and aryl ($C_0$–$C_1$ alkyl)-K-($C_1$–$C_2$ alkyl)-, where K is O or $S(O)_m$ and the aryl is phenyl, pyridyl, naphthyl, indolyl, azaindolyl, benzothienyl, or benzimidazolyl which is optionally substituted by 1–2 $C_1$–$C_4$ alkyl, 1 to 2 halogen, 1 to 2 $-OR^2$, $-S(O)_mR^2$, or $C(O)OR^2$;

$R^2$ is hydrogen, $C_1$–$C_6$ alkyl, or $C_3$–$C_7$ cycloalkyl, and where two $C_1$–$C_6$ alkyl groups are present on one atom they may be optionally joined to form a $C_5$–$C_7$ cyclic ring optionally including oxygen, sulfur or $NR^{3a}$;

$R^4$ and $R^5$ are independently hydrogen, $C_1$–$C_4$ alkyl, or substituted $C_1$–$C_3$ alkyl where the substituents may be 1 to 2 hydroxyl;

X is selected from the group consisting of: $-(CH_2)_qN(R^8)C(O)R^2$, $-(CH_2)_qN(R^8)C(O)R^8$, $-(CH_2)_qN(R^8)C(O)OR^2$, $-(CH_2)_qN(R^8)C(O)OR^8$, $-(CH_2)_qN(R^8)C(O)OR^2$, $-(CH_2)_qN(R^8)C(O)OR^8$, $-(CH_2)_qN(R^2)SO_2R^9$, $-(CH_2)_qN(R^8)SO_2R^8$, $(CH_2)_q N(R^8)SO_2R^2$, $-(CH_2)_qN(R^8)C(O)N(R^2)(R^2)$, $-(CH_2)_qN(R^8)C(O)N(R^2)(R^8)$, $-(CH_2)_qSO_2N(R^2)(R^2)$, $-(CH_2)_qSO_2N(R^2)(R^8)$, $-(CH_2)_qN(R^2)(R^8)$, and $-(CH_2)_qR^{10}$, where the $R^2$, and $(CH_2)_q$ groups may be optionally substituted by 1 to 2 $C_1$–$C_4$ alkyl, hydroxyl, $C_1$–$C_4$ lower alkoxy, carboxyl, $-CONH_2$, $-S(O)_mCH_3$, carboxylate $C_1$–$C_4$ alkyl esters, or 1H-tetrazol-5-yl;

Y is selected from the group consisting of: hydrogen, $C_1$–$C_8$ alkyl, $(CH_2)_t$aryl, $-(CH_2)_qC_5$–$C_7$ cycloalkyl, $-(CH_2)_q-K-(C_1$–$C_6$ alkyl), $-(CH_2)_q-K-(CH_2)_t$aryl, and $-(CH_2)_q-K-(CH_2)_t$ ($C_5$–$C_6$ cycloalkyl), where K is $S(O)_m$ and where the alkyl groups may be optionally substituted by hydroxyl, carboxyl, $CONH_2$, carboxylate $C_1$–$C_4$ alkyl esters or 1H-tetrazole-5-yl and aryl is phenyl, naphthyl, indolyl, pyridyl, thiazolyl, thiopheneyl, pyrazolyl, oxazolyl, isoxazolyl or imidazolyl which may be optionally substituted by 1 to 2 halogen, 1 to 2 $-OR^2$, 1 to 2 $-N(R^2)(R^2)$, $-CO(OR^2)$, 1 to 2 $C_1$–$C_4$ alkyl, $-S(O)_mR^2$, or 1H-tetrazol-5-yl;

A is:

$$-(CH_2)_x-\underset{R^{7a}}{\overset{R^7}{\underset{|}{\overset{|}{C}}}}-(CH_2)_y- \text{ or } -Z-(CH_2)_x-\underset{R^{7a}}{\overset{R^7}{\underset{|}{\overset{|}{C}}}}-(CH_2)_y-$$

where x and y are independantly 0 or 1;

Z is $-N(R^{6a})-$ or $-O-$, where $R^{6a}$ is hydrogen or $C_1$–$C_3$ alkyl;

$R^7$ and $R^{7a}$ are independently hydrogen, $C_1$–$C_6$ alkyl, phenyl, substituted $C_1$–$C_6$ alkyl wherein the substitutent is imidazolyl, naphthyl, phenyl, indolyl, p-hydroxyphenyl, $-OR^2$, $-S(O)_mR^2$, or $R^7$ and $R^{7a}$ can independently be joined to one of $R^4$ or R5 to form alkylene bridges between the terminal nitrogen and the alkyl portions of $R^7$ or $R^{7a}$ groups to form 5 or 6 membered rings; or $R^7$ or $R^{7a}$ can be joined to one another to form a $C_3$–$C_6$ cycloalkyl;

$R^8$ is $-(CH_2)_p$aryl, where aryl is selected from: phenyl, naphthyl, pyridyl, thiazolyl, isothiazolyl, oxaxolyl, isoxazolyl, thienyl, pyrazinyl, pyrimidinyl, benzothienyl, benzofuranyl, benzimidazolyl, imidazolyl, indolyl, quinolinyl, and isoquinolinyl, and where aryl may be substituted by 1 to 2 of halogen, $-R^2$, $-OR^2$, $-N(R^2)(R^2)$, $-C(O)OR^2$, or $-C(O)N(R^2)(R^2)$;

$R^9$ is selected from the group consisting of: isoxazolyl, thiazolyl, isothiazolyl, indolyl, thienyl, benzothienyl, benzofuranyl, benzimidazolyl, imidazolyl, quinolinyl, and isoquinolinyl, which may be substituted by 1 to 2 of halogen, $-R^2$, $-OR^2$, $-N(R^2)(R^2)$, $-C(O)OR^2$, or $-C(O)N(R^2)(R^2)$;

$R^{10}$ is selected form the group consisting of: 1,2,4-oxadiazolyl, pyrazinyl, and triazolyl which may be substituted by $-R^2$, $-OR^2$, or $-N(R^2)(R^2)$;

m is 0, 1, or 2;

p is 0, 1, or 2 q is 0, 1, or 2;

t is 0, 1, or 2;

and pharmaceutically acceptable salts and individual diastereomers thereof.

4. A compound of the formula:

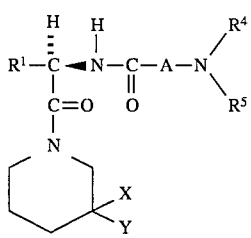 Formula Ic wherein:

R¹ is selected from the group consisting of:

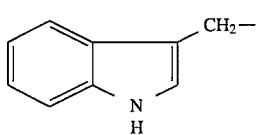

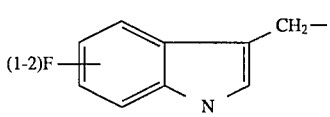

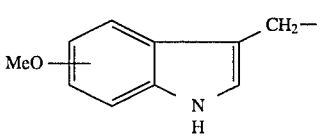

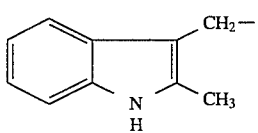

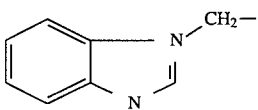

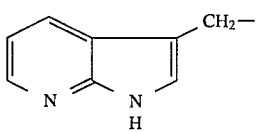

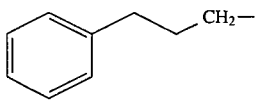

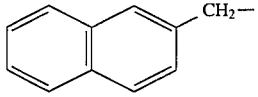

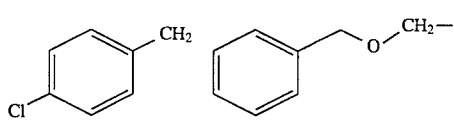

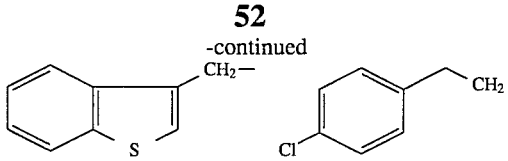

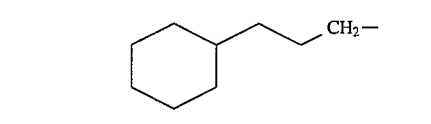

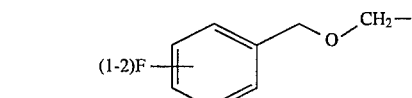

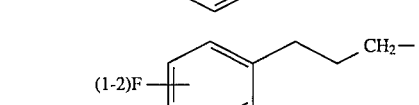

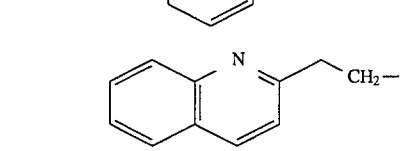

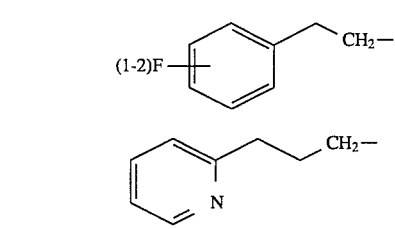

or their regioisomers where not specified;

R² is hydrogen, $C_1$–$C_6$ alkyl, or $C_3$–$C_7$ cycloalkyl and where two $C_1$–$C_6$ alkyl groups are present on one atom they may be optionally joined to form a $C_5$–$C_7$ cyclic ring optionally including oxygen, sulfur or $NR_{3a}$;

R⁴ and R⁵ are independently selected from the group consisting of:

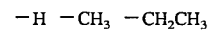

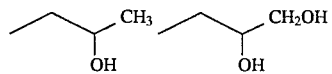

X is selected from the group consisting of:
—$(CH_2)_qN(R^8)C(O)R^2$,    —$(CH_2)_qN(R^8)C(O)R^8$,
—$(CH_2)_qN(R^8)C(O)OR^2$,   —$(CH_2)_qN(R^2)C(O)OR^8$,
—$(CH_2)_qN(R^8)C(O)OR^8$,   —$(CH_2)_qN(R^2)SO_2R^9$,
—$(CH_2)_q$ $N(R^8)SO_2R^8$, —$(CH_2)_qN(R^8)SO_2R^2$,
—$(CH_2)_qN(R^2)SO_2N(R^2)(R^8)$,
—$(CH_2)_qN(R^8)C(O)N(R^2)(R^2)$,
—$(CH_2)_qN(R^8)C(O)N(R^2)(R^8)$,    and
—$(CH_2)_qN(R^2)(R_8)$;

Y is selected from the group consisting of: hydrogen,

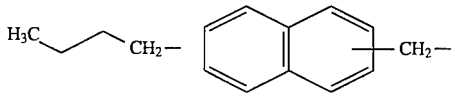

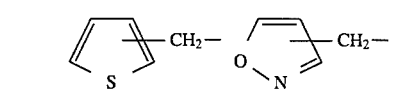

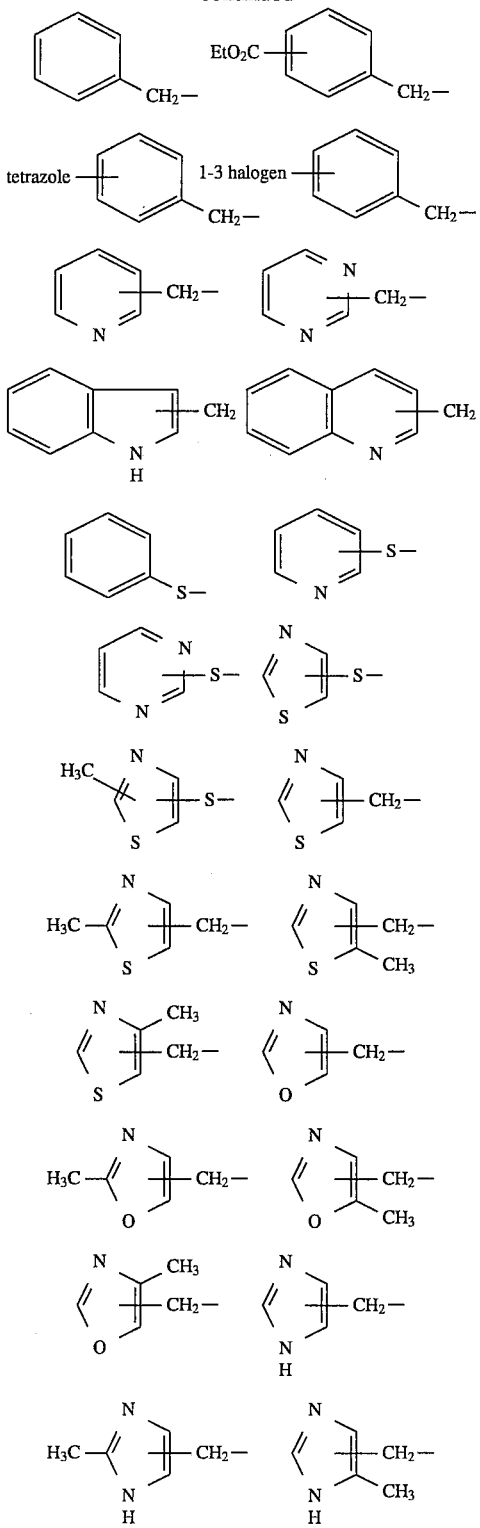

or their regioisomers whereof where not specified;
A is:

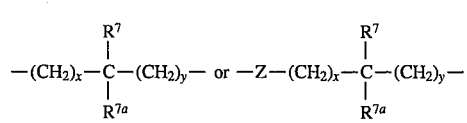

where x and y are independently 0 or 1;

Z is —(NR$^{6a}$)— or —O—, where R$^{6a}$ is hydrogen or C$_1$-C$_6$ alkyl;

R$^7$ and R$^{7a}$ are independently C$_1$-C$_6$ alkyl and substituted C$_1$-C$_6$ alkyl wherein the substituent is phenyl, naphthyl or indolyl or R$^7$ and R$^{7a}$ can independently be joined to one of the R$^4$ or R$^5$ to form alkylene bridges between the terminal nitrogen and the alkyl portions of R$^7$ or R$^{7a}$ to form 5 or 6 membered rings;

R$^8$ is (CH$_2$)$_p$aryl where aryl is selected from: phenyl, naphthyl, pyridyl, pyrazinyl, pyrimidinyl, thiazolyl, indolyl, quinolinyl and isoquinolinyl and where the aryl may be substituted by 1 to 2 halogen, —R$^2$, —OR$^2$, N(R$^2$)(R$^2$), —C(O)OR$^2$ or —C(O)N(R$^2$)(R$^2$);

R$^9$ is selected from the group consisting of: isoxazolyl, thiazolyl, indolyl, quinolinyl and isoquinolinyl, which may be substituted by 1 to 2 halogen, —R$^2$, —OR$^2$, —N(R$^2$)(R$^2$), —C(O)OR$^2$ or —C(O)N(R$^2$)(R$^2$);

R$^{10}$ is 1,2,4-oxadiazolyl which may be substituted by —R$^2$, —OR$^2$, or —N(R$^2$)(R$^2$);

m is 0, 1 or 2;

p is 0 or 1;

q is 0 or 1;

t is 0 or 1;

and pharmaceutically acceptable salts and individual diastereomers thereof.

5. A compound of the formula:

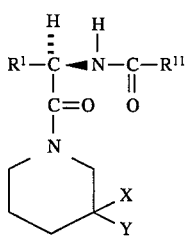

Formula Id wherein:

R$^1$ is selected from the group consisting of:

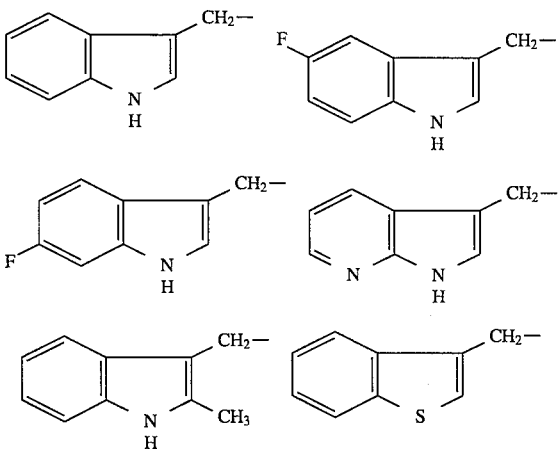

X is selected from the group consisting of:

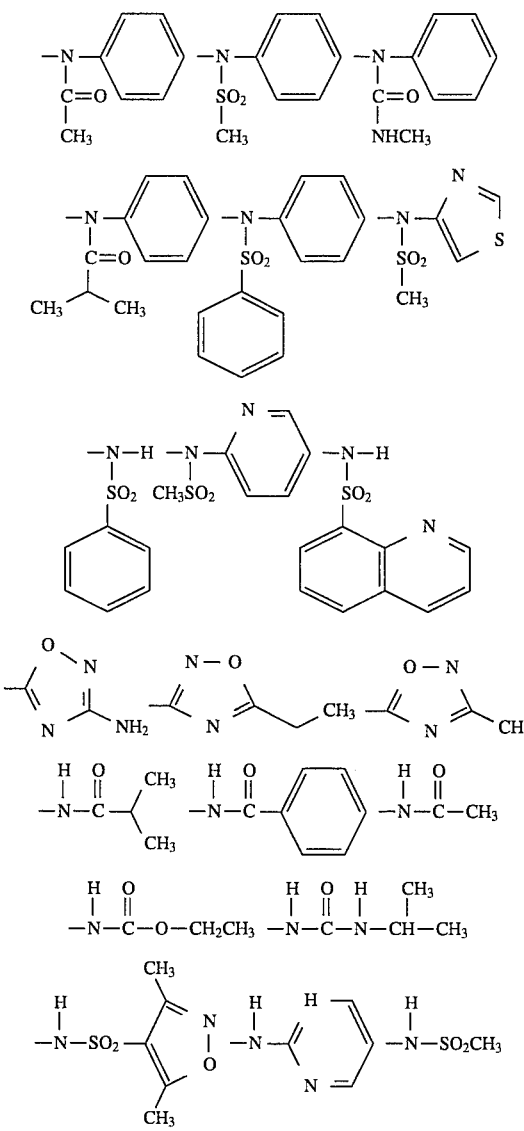

Y is selected from the group consisting of: hydrogen,

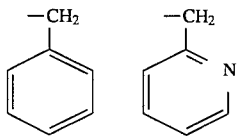

-continued

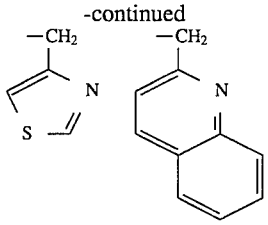

$R^{11}$ is selected from the group consisting of:

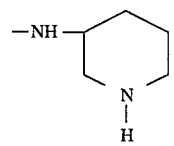
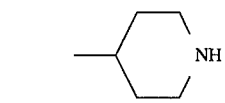
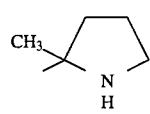
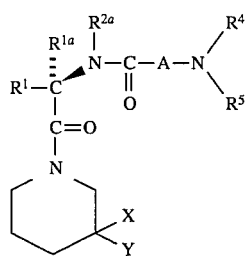

and pharmaceutically acceptable salts and individual diastereomers thereof.

6. The stereospecifically defined compound of claim 1 of the formula:

$$R^1-C\begin{matrix}R^{1a}\\\vdots\\C=O\\|\\N\end{matrix}\begin{matrix}R^{2a}\\|\\N-C-A-N\\\|\\O\end{matrix}\begin{matrix}R^4\\/\\\backslash R^5\end{matrix}$$

wherein $R^1$, $R^{1a}$, $R^{2a}$, $R^4$, $R^5$, A, X, and Y are as defined in claim 1.

7. A pharmaceutical composition which comprises an inert carrier and an effective amount of a compound of claim 1.

8. A method for increasing levels of endogenous growth hormone in a human or an animal which comprises administering to such human or animal an effective amount of a compound of claim 1.

* * * * *